United States Patent
Nabeta

(10) Patent No.: US 9,308,195 B2
(45) Date of Patent: *Apr. 12, 2016

(54) NON-AQUEOUS TAXANE FORMULATIONS AND METHODS OF USING THE SAME

(71) Applicant: Teikoku Pharma USA, Inc., San Jose, CA (US)

(72) Inventor: Kiichiro Nabeta, Tokyo (JP)

(73) Assignee: Teikoku Pharma USA, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/564,384

(22) Filed: Dec. 9, 2014

(65) Prior Publication Data

US 2015/0094361 A1    Apr. 2, 2015

Related U.S. Application Data

(63) Continuation of application No. 14/041,675, filed on Sep. 30, 2013, now Pat. No. 8,940,786.

(60) Provisional application No. 61/708,595, filed on Oct. 1, 2012, provisional application No. 61/708,586, filed on Oct. 1, 2012.

(51) Int. Cl.
| | |
|---|---|
| *A61K 31/337* | (2006.01) |
| *A61K 9/10* | (2006.01) |
| *A61K 47/10* | (2006.01) |
| *A61K 47/12* | (2006.01) |
| *A61K 47/14* | (2006.01) |
| *A61K 47/26* | (2006.01) |
| *A61K 47/44* | (2006.01) |

(52) U.S. Cl.
CPC ............ *A61K 31/337* (2013.01); *A61K 9/10* (2013.01); *A61K 47/10* (2013.01); *A61K 47/12* (2013.01); *A61K 47/14* (2013.01); *A61K 47/26* (2013.01); *A61K 47/44* (2013.01)

(58) Field of Classification Search
CPC .............................. A61K 9/10; A61K 31/337
USPC ......................................................... 514/449
See application file for complete search history.

(56) References Cited

U.S. PATENT DOCUMENTS

| | | |
|---|---|---|
| 4,814,470 A | 3/1989 | Colin et al. |
| 5,399,363 A | 3/1995 | Liversidge et al. |
| 5,403,858 A | 4/1995 | Bastard et al. |
| 5,407,683 A | 4/1995 | Shively |
| 5,415,869 A | 5/1995 | Straubinger et al. |
| 5,438,072 A | 8/1995 | Bobee et al. |
| 5,439,686 A | 8/1995 | Desai et al. |
| 5,498,421 A | 3/1996 | Grinstaff et al. |
| 5,560,933 A | 10/1996 | Soon-shiong et al. |
| 5,607,690 A | 3/1997 | Akazawa |
| 5,616,330 A | 4/1997 | Kaufman et al. |
| 5,626,867 A | 5/1997 | Eibl et al. |
| 5,698,582 A | 12/1997 | Bastart et al. |
| 5,714,512 A | 2/1998 | Bastart et al. |
| 5,723,635 A | 3/1998 | Durand et al. |
| 5,733,888 A | 3/1998 | Carver et al. |
| 5,750,561 A | 5/1998 | Bastart et al. |
| 5,770,222 A | 6/1998 | Unger et al. |
| 5,785,976 A | 7/1998 | Westesen et al. |
| 5,858,410 A | 1/1999 | Muller et al. |
| 5,877,205 A | 3/1999 | Andersson |
| 5,902,610 A | 5/1999 | Hausheer et al. |
| 5,925,669 A | 7/1999 | Katz et al. |
| 5,929,030 A | 7/1999 | Hamied et al. |
| 5,965,603 A | 10/1999 | Johnson et al. |
| 5,968,972 A | 10/1999 | Broder et al. |
| 5,972,992 A | 10/1999 | Carver et al. |
| 5,977,164 A | 11/1999 | Carver et al. |
| 6,008,385 A | 12/1999 | Durand et al. |
| 6,017,948 A | 1/2000 | Rubinfeld et al. |
| 6,022,985 A | 2/2000 | Authelin et al. |
| 6,071,952 A | 6/2000 | Owens et al. |
| 6,090,844 A | 7/2000 | Han et al. |

(Continued)

FOREIGN PATENT DOCUMENTS

| | | |
|---|---|---|
| CN | 101244053 A | 2/2007 |
| CN | 100998560 A | 7/2007 |

(Continued)

OTHER PUBLICATIONS

U.S. Appl. No. 14/041,694, filed Sep. 30, 2013, Nabeta.
Chen, Jie, "Preparation, Characterization and in Vitro Evaluation of Solid Dispersions Containing Docetaxel," Drug Development and Industrial Pharmacy (2008), 34(6):588-594.
Dev et al., "Isolation and characterization of impurities in docetaxel," Journal of Pharmaceutical and Biomedical Analysis (2006), 40(3):614-622.
Diaz et al., "Changes in microtubule protofilament number induced by Taxol binding to an easily accessible site. Internal microtubule dynamics," Journal of Biological Chemistry (1998), 273(50):33803-33810.
Ekins et al,. "Accelerated Communication, A pharmacophore for human pregnane X receptor ligands," Drug Metabolism and Disposition (2002), 30(1):96-99.
Gentile et al., "Synthesis of dimeric and tetrameric macrolactams with cytotoxic activity," Canadian Journal of Chemistry (2000), 78(6):925-934.
Han et al., "Phytantriol-based inverted type bicontinuous cubic phase for vascular embolization and drug sustained release," European Journal of Pharmaceutical Sciences (2010), 41(5):692-699.

(Continued)

*Primary Examiner* — Raymond Henley, III
(74) *Attorney, Agent, or Firm* — Foley & Lardner LLP

(57) ABSTRACT

Non-aqueous, ethanol-free taxane formulations are provided. Formulations of embodiments of the invention include a taxane, an oil, a non-ionic surfactant, a non-aqueous solvent, and an organic acid component, wherein the organic acid component is soluble in the non-aqueous solvent and the amount by weight of non-ionic surfactant is equal to or greater than the amount by weight of non-aqueous solvent. Also provided are methods of using the formulations, as well as kits that include the formulations. Non-aqueous, ethanol-free docetaxel formulations are provided. Formulations of embodiments of the invention include docetaxel, an oil, a non-ionic surfactant, a non-aqueous solvent, and an organic acid which is soluble in the non-aqueous solvent and is substantially free of any conjugate base. Also provided are methods of using the formulations, as well as kits that include the formulations.

51 Claims, No Drawings

(56) References Cited

U.S. PATENT DOCUMENTS

| | | | |
|---|---|---|---|
| 6,090,955 A | 7/2000 | Reszka et al. |
| 6,096,331 A | 8/2000 | Desai et al. |
| 6,107,333 A | 8/2000 | Andersson |
| 6,118,011 A | 9/2000 | Mayhew et al. |
| 6,121,234 A | 9/2000 | Benet et al. |
| 6,121,245 A | 9/2000 | Firshein |
| 6,121,313 A | 9/2000 | Gao et al. |
| 6,136,846 A | 10/2000 | Rubinfeld et al. |
| 6,153,644 A | 11/2000 | Owens et al. |
| 6,197,980 B1 | 3/2001 | Durand et al. |
| 6,207,178 B1 | 3/2001 | Westesen et al. |
| 6,218,374 B1 | 4/2001 | Rubinfield |
| 6,231,887 B1 | 5/2001 | Gao et al. |
| 6,267,985 B1 | 7/2001 | Chen et al. |
| 6,284,268 B1 | 9/2001 | Mishra et al. |
| 6,294,192 B1 | 9/2001 | Patel et al. |
| 6,334,445 B1 | 1/2002 | Mettinger |
| 6,346,233 B1 | 2/2002 | Knight et al. |
| 6,348,215 B1 | 2/2002 | Straubinger et al. |
| 6,348,491 B1 | 2/2002 | Chu et al. |
| 6,391,832 B2 | 5/2002 | Lyons et al. |
| 6,436,430 B1 | 8/2002 | Mulye |
| 6,451,339 B2 | 9/2002 | Patel et al. |
| 6,458,373 B1 | 10/2002 | Lambert et al. |
| 6,500,461 B2 | 12/2002 | Perkins et al. |
| 6,506,405 B1 | 1/2003 | Desai et al. |
| 6,509,370 B1 | 1/2003 | Joshi-Hangal et al. |
| 6,531,139 B1 | 3/2003 | Gao et al. |
| 6,537,579 B1 | 3/2003 | Desai et al. |
| 6,538,019 B1 | 3/2003 | Nakajima et al. |
| 6,538,020 B2 | 3/2003 | Joshi-Hangal et al. |
| 6,605,298 B1 | 8/2003 | Leigh et al. |
| 6,610,317 B2 | 8/2003 | Straub et al. |
| 6,638,522 B1 | 10/2003 | Mulye |
| 6,638,973 B2 | 10/2003 | Holton |
| 6,660,286 B1 | 12/2003 | Lambert et al. |
| 6,667,048 B1 | 12/2003 | Lambert et al. |
| 6,720,001 B2 | 4/2004 | Chen et al. |
| 6,727,280 B2 | 4/2004 | Palepu et al. |
| 6,749,868 B1 | 6/2004 | Desai et al. |
| 6,753,006 B1 | 6/2004 | Desai et al. |
| 6,761,901 B1 | 7/2004 | Betageri et al. |
| 6,761,903 B2 | 7/2004 | Chen et al. |
| 6,815,642 B2 | 11/2004 | Haag |
| 6,828,346 B2 | 12/2004 | Joshi-Hangal et al. |
| 6,838,569 B2 | 1/2005 | Sharma et al. |
| 6,932,983 B1 | 8/2005 | Straub et al. |
| 6,964,946 B1 | 11/2005 | Gutierrez-Rocca et al. |
| 6,979,456 B1 | 12/2005 | Parikh et al. |
| 6,982,282 B2 | 1/2006 | Lambert et al. |
| 7,030,155 B2 | 4/2006 | Lambert et al. |
| 7,060,285 B2 | 6/2006 | Muller |
| 7,064,201 B2 | 6/2006 | Hayashi et al. |
| 7,074,821 B1 | 7/2006 | Bouchard et al. |
| 7,101,568 B2 | 9/2006 | Dang et al. |
| 7,345,093 B2 | 3/2008 | Augustine et al. |
| 7,387,623 B2 | 6/2008 | Macleod |
| 7,387,791 B2 | 6/2008 | Betageri et al. |
| RE40,493 E | 9/2008 | Straub et al. |
| 7,446,126 B2 | 11/2008 | Gabetta et al. |
| 7,662,980 B2 | 2/2010 | Liao et al. |
| 7,674,903 B2 | 3/2010 | Hayashi et al. |
| 7,744,909 B2 | 6/2010 | Muller |
| 7,771,751 B2 | 8/2010 | Desai et al. |
| 7,838,551 B2 | 11/2010 | Santini et al. |
| 7,919,113 B2 | 4/2011 | Domb |
| 7,919,497 B2 | 4/2011 | Palladino et al. |
| 7,935,704 B2 | 5/2011 | Palladino et al. |
| 7,956,058 B2 | 6/2011 | Hayashi et al. |
| 8,044,093 B2 | 10/2011 | Hao |
| 8,163,940 B2 | 4/2012 | Pyo et al. |
| 8,318,957 B2 | 11/2012 | Gabetta et al. |
| 8,940,786 B2 * | 1/2015 | Nabeta .................. 514/449 |
| 2001/0029264 A1 | 10/2001 | McChesney-Harris |
| 2002/0013298 A1 | 1/2002 | Hunter |
| 2002/0034537 A1 | 3/2002 | Schulze et al. |
| 2002/0058616 A1 | 5/2002 | Broder et al. |
| 2002/0102280 A1 | 8/2002 | Anderson |
| 2002/0141966 A1 | 10/2002 | Dang |
| 2003/0099674 A1 | 5/2003 | Chen |
| 2003/0133955 A1 | 7/2003 | Desai et al. |
| 2003/0133984 A1 | 7/2003 | Ambuhl et al. |
| 2003/0158249 A1 | 8/2003 | Chi et al. |
| 2003/0219472 A1 | 11/2003 | Pauletti et al. |
| 2004/0092428 A1 | 5/2004 | Chen et al. |
| 2004/0105778 A1 | 6/2004 | Lee et al. |
| 2004/0122081 A1 | 6/2004 | Gogate et al. |
| 2004/0219214 A1 | 11/2004 | Gravett et al. |
| 2004/0220081 A1 | 11/2004 | Kreitz et al. |
| 2005/0025792 A1 | 2/2005 | Peracchia et al. |
| 2005/0070496 A1 | 3/2005 | Borovac et al. |
| 2005/0090667 A1 | 4/2005 | Hayashi et al. |
| 2005/0197344 A1 | 9/2005 | Palladino et al. |
| 2006/0067952 A1 | 3/2006 | Chen |
| 2006/0079571 A1 | 4/2006 | Gabetta et al. |
| 2006/0188566 A1 | 8/2006 | Liversidge et al. |
| 2006/0210622 A1 | 9/2006 | Pace et al. |
| 2006/0217553 A1 | 9/2006 | Hayashi et al. |
| 2006/0223822 A1 | 10/2006 | Hayashi et al. |
| 2006/0223823 A1 | 10/2006 | Hayashi et al. |
| 2006/0241170 A1 | 10/2006 | Soon-Shiong et al. |
| 2006/0292186 A1 | 12/2006 | Garrigue et al. |
| 2007/0078138 A1 | 4/2007 | Palladino et al. |
| 2007/0082838 A1 | 4/2007 | De et al. |
| 2007/0117744 A1 | 5/2007 | Desai et al. |
| 2007/0142457 A1 | 6/2007 | Pontiroli et al. |
| 2007/0196361 A1 | 8/2007 | Soon-Shiong et al. |
| 2007/0225510 A1 | 9/2007 | Henri et al. |
| 2007/0264349 A1 | 11/2007 | Lee et al. |
| 2008/0045584 A1 | 2/2008 | Chi et al. |
| 2008/0051450 A1 | 2/2008 | Santini et al. |
| 2008/0057129 A1 | 3/2008 | Lerner et al. |
| 2008/0064760 A1 | 3/2008 | Li et al. |
| 2008/0108693 A1 | 5/2008 | Liao et al. |
| 2008/0167369 A1 | 7/2008 | Gabetta et al. |
| 2008/0187595 A1 | 8/2008 | Jordan et al. |
| 2008/0200700 A1 | 8/2008 | Gabetta et al. |
| 2008/0220074 A1 | 9/2008 | Bosch et al. |
| 2008/0262078 A1 | 10/2008 | Namdeo et al. |
| 2008/0300297 A1 | 12/2008 | Kysilka |
| 2008/0319048 A1 | 12/2008 | Palepu et al. |
| 2009/0011005 A1 | 1/2009 | Zago et al. |
| 2009/0011009 A1 | 1/2009 | Benita et al. |
| 2009/0018353 A1 | 1/2009 | Pyo et al. |
| 2009/0118354 A1 | 5/2009 | Liu et al. |
| 2009/0130198 A1 | 5/2009 | Hao et al. |
| 2009/0143997 A1 | 6/2009 | Yaffe et al. |
| 2009/0156660 A1 | 6/2009 | Svoboda et al. |
| 2009/0156828 A1 | 6/2009 | Henri et al. |
| 2009/0163574 A1 | 6/2009 | Kim et al. |
| 2009/0215882 A1 | 8/2009 | Bouzada et al. |
| 2009/0221688 A1 | 9/2009 | Machado et al. |
| 2009/0238878 A1 | 9/2009 | Singh |
| 2009/0275647 A1 | 11/2009 | Sehgal et al. |
| 2009/0275762 A1 | 11/2009 | Liao et al. |
| 2009/0298926 A1 | 12/2009 | Gabetta et al. |
| 2009/0306400 A1 | 12/2009 | Henri et al. |
| 2010/0034749 A1 | 2/2010 | Schulze et al. |
| 2010/0069643 A1 | 3/2010 | McChesney et al. |
| 2010/0099879 A1 | 4/2010 | Benovsky et al. |
| 2010/0099897 A1 | 4/2010 | Kim et al. |
| 2010/0111830 A1 | 5/2010 | Boyden et al. |
| 2010/0111831 A1 | 5/2010 | Boyden et al. |
| 2010/0111837 A1 | 5/2010 | Boyden et al. |
| 2010/0111841 A1 | 5/2010 | Boyden et al. |
| 2010/0111842 A1 | 5/2010 | Boyden et al. |
| 2010/0111843 A1 | 5/2010 | Boyden et al. |
| 2010/0111844 A1 | 5/2010 | Boyden et al. |
| 2010/0111845 A1 | 5/2010 | Boyden et al. |
| 2010/0111846 A1 | 5/2010 | Boyden et al. |
| 2010/0111847 A1 | 5/2010 | Boyden et al. |
| 2010/0111848 A1 | 5/2010 | Boyden et al. |
| 2010/0111849 A1 | 5/2010 | Boyden et al. |
| 2010/0111850 A1 | 5/2010 | Boyden et al. |

(56) References Cited

U.S. PATENT DOCUMENTS

| | | |
|---|---|---|
| 2010/0111854 A1 | 5/2010 | Boyden et al. |
| 2010/0111855 A1 | 5/2010 | Boyden et al. |
| 2010/0111938 A1 | 5/2010 | Boyden et al. |
| 2010/0112067 A1 | 5/2010 | Boyden et al. |
| 2010/0112068 A1 | 5/2010 | Boyden et al. |
| 2010/0113614 A1 | 5/2010 | Boyden et al. |
| 2010/0113615 A1 | 5/2010 | Boyden et al. |
| 2010/0114267 A1 | 5/2010 | Boyden et al. |
| 2010/0114268 A1 | 5/2010 | Boyden et al. |
| 2010/0114496 A1 | 5/2010 | Boyden et al. |
| 2010/0114497 A1 | 5/2010 | Boyden et al. |
| 2010/0114546 A1 | 5/2010 | Boyden et al. |
| 2010/0119557 A1 | 5/2010 | Boyden et al. |
| 2010/0121466 A1 | 5/2010 | Boyden et al. |
| 2010/0143243 A1 | 6/2010 | Boyden et al. |
| 2010/0145080 A1 | 6/2010 | Johnson et al. |
| 2010/0152651 A1 | 6/2010 | Boyden et al. |
| 2010/0152880 A1 | 6/2010 | Boyden et al. |
| 2010/0160653 A1 | 6/2010 | Palle et al. |
| 2010/0163576 A1 | 7/2010 | Boyden et al. |
| 2010/0166872 A1 | 7/2010 | Singh et al. |
| 2010/0168900 A1 | 7/2010 | Boyden et al. |
| 2010/0185174 A1 | 7/2010 | Boyden et al. |
| 2010/0187728 A1 | 7/2010 | Boyden et al. |
| 2010/0197776 A1 | 8/2010 | Didier et al. |
| 2010/0197944 A1 | 8/2010 | Palle et al. |
| 2010/0267818 A1 | 10/2010 | Yoo et al. |
| 2010/0286254 A1 | 11/2010 | Blatter et al. |
| 2010/0297244 A1 | 11/2010 | Khopade et al. |
| 2010/0311825 A1 | 12/2010 | Rortais et al. |
| 2011/0002851 A1 | 1/2011 | Haas et al. |
| 2011/0082193 A1 | 4/2011 | Kysilka |
| 2011/0105598 A1 | 5/2011 | Gurjar et al. |
| 2011/0112036 A1 | 5/2011 | Demeule et al. |
| 2011/0118199 A1 | 5/2011 | Dormeyer |
| 2011/0130446 A1 | 6/2011 | Parente Duena et al. |
| 2011/0150765 A1 | 6/2011 | Boyden et al. |
| 2011/0152360 A1 | 6/2011 | Liu et al. |
| 2011/0159111 A1 | 6/2011 | Curry et al. |
| 2011/0189125 A1 | 8/2011 | George et al. |
| 2011/0195030 A1 | 8/2011 | Mumper et al. |
| 2011/0196026 A1 | 8/2011 | De et al. |
| 2011/0206739 A1 | 8/2011 | Nicolosi et al. |
| 2011/0245260 A1 | 10/2011 | Palladino et al. |
| 2011/0275705 A1 | 11/2011 | Daftary et al. |
| 2011/0275841 A1 | 11/2011 | Kadaboina et al. |
| 2011/0293745 A1 | 12/2011 | Hoch et al. |
| 2012/0058151 A1 | 3/2012 | Gonzalez Ferreiro et al. |
| 2012/0071674 A1 | 3/2012 | Cieslinski |
| 2012/0087959 A1 | 4/2012 | Khopade et al. |
| 2012/0101738 A1 | 4/2012 | Boyden et al. |
| 2012/0109613 A1 | 5/2012 | Boyden et al. |
| 2012/0128783 A1 | 5/2012 | Boyden et al. |
| 2012/0157517 A1 | 6/2012 | Chen et al. |
| 2012/0164069 A1 | 6/2012 | Boyden et al. |
| 2012/0164072 A1 | 6/2012 | Linder et al. |
| 2012/0225118 A1 | 9/2012 | Chen et al. |
| 2012/0295802 A1 | 11/2012 | Yaffe et al. |
| 2013/0052241 A1 | 2/2013 | Nabeta |

FOREIGN PATENT DOCUMENTS

| | | |
|---|---|---|
| CN | 101525321 | 9/2009 |
| EP | 1479382 A1 | 11/2004 |
| JP | 04-164024 A | 6/1992 |
| JP | 2595458 B2 | 1/1997 |
| JP | 09-507233 A | 7/1997 |
| JP | 2010-270023 | 12/2010 |
| JP | 4734910 B2 | 5/2011 |
| WO | WO 93/23389 A1 | 11/1993 |
| WO | WO 94/18954 A1 | 9/1994 |
| WO | WO 94/20072 A1 | 9/1994 |
| WO | WO 98/30205 A1 | 7/1998 |
| WO | WO 99/00113 A1 | 1/1999 |
| WO | WO 99/56727 A2 | 11/1999 |
| WO | WO 00/32186 A3 | 6/2000 |
| WO | WO 00/33862 A1 | 6/2000 |
| WO | WO 00/78247 A1 | 12/2000 |
| WO | WO 01/30448 A1 | 5/2001 |
| WO | WO 01/72299 A1 | 10/2001 |
| WO | WO 01/76561 A3 | 10/2001 |
| WO | WO 2004/105737 A3 | 12/2004 |
| WO | WO 2007/096900 A1 | 8/2007 |
| WO | WO 2008/026048 A3 | 3/2008 |
| WO | WO 2008/087076 A1 | 7/2008 |
| WO | WO 2008/102374 A1 | 8/2008 |
| WO | WO 2008/114274 A1 | 9/2008 |
| WO | WO 2009/004188 A3 | 1/2009 |
| WO | WO 2009/043226 A1 | 4/2009 |
| WO | WO 2009/123595 A1 | 10/2009 |
| WO | WO 2010/023321 A1 | 3/2010 |
| WO | WO 2011/081373 A2 | 7/2011 |
| WO | WO 2012/160568 A1 | 11/2012 |

OTHER PUBLICATIONS

Harper et al., "13C NMR Investigation of Solid-State Polymorphism in 10-Deacetyl Baccatin III," Journal of the American Chemical Society (2002), 124(35):10589-10595.

Jimenez-Barbero et al., "The solid state, solution and tubulin-bound conformations of agents that promote microtubule stabilization," Current Medicinal Chemistry: Anti-Cancer Agents (2002), 2(1):91-122.

Johnson et al., 12,13-Isotaxanes: Synthesis of New Potent Analogs and X-ray Crystallographic Confirmation of Structure, Journal of Medicinal Chemistry (1997), 40(18), 2810-2812 CODEN: JMCMAR; ISSN: 0022-2623.

Juarez-Guerra et al., "Addition reaction of benzylbenzylideneamine to lithium enolates of 1,3-dioxolan-4-one: synthesis of 2-phenylisoserines," ARKIVOC (2011), (9):354-366.

Lucatelli et al., "Synthesis of C-3' Methyl Taxotere (Docetaxel)," Journal of Organic Chemistry (2002), 67(26):9468-9470.

Muller et al., "'Abnormal' eight-membered ring formation through SN2' intramolecular Nozaki/Kishi reaction in a synthetic approach to a taxane precursor," Tetrahedron Letters (1998), 39(3/4):279-282.

Naik et al., "Preparation of PEGylated liposomes of docetaxel using supercritical fluid technology," Journal of Supercritical Fluids (2010), 54(1):110-119.

Perrin, M.A., "Crystallography of drug polymorphism: emergence of new resolution methods and prediction of crystalline structures," Annales Pharmaceutiques Francaises (2002), 60(3):187-202, with English summary on first page.

Qi et al., "A novel method to synthesize docetaxel and its isomer with high yields," Journal of Heterocyclic Chemistry (2005), 42(4):679-684.

Raczko et al., "Asymmetric syn-dihydroxylation of β-substituted (2R)-N-(α,β-enoyl)bornane-10,2-sultams," Helvetica Chimica Acta (1998), 81(7):1264-1277.

Roy et al., "A concise enantioselective synthesis of a fully oxygen substituted ring A Taxol precursor," Tetrahedron (2003), 59(27):5115-5121.

Skariyachan et al., "Design and discovery of novel therapeutic drugs against Helicobacter pylori gastroduodenal cancer by in silico approach," Research Journal of Pharmaceutical, Biological and Chemical Sciences (2010), 1(4):1005-1016.

Skariyachan et al., "In silico investigation and docking studies of E2F3 tumor marker: discovery and evaluation of potential inhibitors for prostate and breast cancer," International Journal of Pharmaceutical Sciences and Drug Research (2010), 2(4):254-260.

(56) References Cited

OTHER PUBLICATIONS

Wang et al., "Preparation and evaluation of docetaxel-loaded albumin nanoparticles for intravenous administration," Journal of Chinese Pharmaceutical Sciences (2010), 19(3):214-222.

Zaske et al., "Docetaxel. Solid state characterization by x-ray powder diffraction and thermogravimetry," Journal de Physique IV: Proceedings (2001), 11(Pr10, XXVII JEEP, Journees d'Etude des Equilibres entre Phases, 2001), 221-226.

Gao et al., "Preparation and Characterization of a Submicron Lipid Emulsion of Docetaxel: Submicron Lipid Emulsion of Docetaxel," Drug Development and Industrial Pharmacy, 2008, 34:1227-1237.

Zhao et al., "Evaluation of Docetaxel-Loaded Intravenous Lipid Emulsion: Pharmacokinetics, Tissue Distribution, Antitumor Activity, Safety and Toxicity," Pharm. Res., 2010, 27:1687-1702.

"Carbowax Polyethylene Glycols," Dow Chemical (evidentiary reference), date unknown, U.S. Appl. No. 14/041,694 with Jan. 26, 2015 Office Action.

* cited by examiner

NON-AQUEOUS TAXANE FORMULATIONS AND METHODS OF USING THE SAME

This application is a Continuation of U.S. application Ser. No. 14/041,675, filed Sep. 30, 2013, which claims priority from U.S. Provisional Applications 61/708,595 and 61/708,586, both filed Oct. 1, 2012, and each incorporated herein by reference in its entirety.

Taxanes constitute a family of naturally occurring diterpene compounds including paclitaxel. Paclitaxel, originally isolated from the bark of the Pacific Yew tree (*Taxus brevifolia*), and its semi-synthetic analogue, docetaxel, are two examples of taxane compounds. Taxanes are active agents that block cell growth by stopping mitosis via microtubule interference.

Taxanes can be used effectively to treat a variety of cancers and have been reported to have therapeutic effects in treating certain inflammatory diseases. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11-18; The Pharmacological Basis of Therapeutics (Goodman Gilman et al., eds.), Pergamon Press, New York (1990), p. 1239: Suffness, Antitumor Alkaloids, in: "The Alkaloids, Vol. XXV," Academic Press, Inc. (1985), Chapter 1, pp. 6-18: Rizzo et al., J. Pharm. & Biomed. Anal. 8(2):159-164 (1990); and Biotechnology 9:933-938 (October, 1991).

Formulation of taxanes in therapeutically useful carriers, so as to enable the taxanes to be administered to animals, is made difficult by the nature of the taxane molecule, which can be poorly soluble in both aqueous and lipid carriers.

Docetaxel is an antineoplastic agent belonging to the taxoid family. It is prepared by semisynthesis beginning with a precursor extracted from the renewable needle biomass of yew plants. The chemical name for docetaxel is (2R,3S)-N-carboxy-3-phenylisoserine,Ntert-butyl ester, 13-ester with 5β-20-epoxy-1,2α,4,7β,10β,13α-hexahydroxytax-11-en-9-one 4-acetate 2-benzoate. Docetaxcel has the following structural formula:

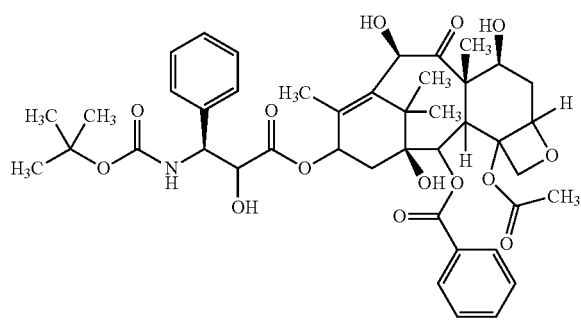 [SMILES: CC(=O)OC12COC1C[C@H](O)[C@@]1(C)C(=O)[C@H](O)C3=C(C)C(OC(=O)C(O)[C@@H](NC(=O)OC(C)(C)C)c4ccccc4)C[C@@](O)(C(OC(=O)c4ccccc4)C21)C3(C)C]

Docetaxel can be used effectively to treat a variety of cancers and has been reported to have a therapeutic effect in treating certain inflammatory diseases. For example, docetaxel has been found to have activity against breast cancer, non-small cell lung cancer, prostate cancer, gastric adenocarcinoma and head and neck cancer.

However, docetaxel is highly lipophilic and practically insoluble in water. This makes the formulation of docetaxel in therapeutically useful carriers a challenge.

SUMMARY

Non-aqueous, ethanol-free taxane liquid nanodispersion formulations are provided. The nanodispersion formulations include a taxane, an oil, a non-ionic surfactant, a non-aqueous solvent, and an organic acid component, wherein the organic acid component is soluble in the non-aqueous solvent and the amount by weight of non-ionic surfactant is equal to or greater than the amount by weight of non-aqueous solvent. Also provided are methods of using the nanodispersion formulations, as well as kits that include the nanodispersion formulations.

Non-aqueous, ethanol-free taxane liquid nanodispersion formulations are provided. The nanodispersion formulations include a taxane, an oil, a non-ionic surfactant, a non-aqueous solvent, and an organic acid component, wherein the organic acid component is soluble in the non-aqueous solvent and the amount by weight of non-ionic surfactant is equal to or greater than the amount by weight of non-aqueous solvent. Also provided are methods of using the nanodispersion formulations, as well as kits that include the nanodispersion formulations. Additionally, provided herein is a non-aqueous, ethanol-free docetaxel liquid nanodispersion formulation comprising docetaxel, an oil, a non-ionic surfactant, a non-aqueous solvent and an organic acid, wherein said organic acid is soluble in the non-aqueous solvent and is substantially free of any conjugate base. Also provided are methods of using the nanodispersion formulations, as well as kits that include the nanodispersion formulations.

DETAILED DESCRIPTION

Taxane Nanodispersion Formulations

Non-aqueous, ethanol-free taxane liquid nanodispersion formulations are provided. The nanodispersion formulations include a taxane, an oil, a non-ionic surfactant, a non-aqueous solvent, and an organic acid component, wherein the organic acid component is soluble in the non-aqueous solvent and the amount by weight of non-ionic surfactant is equal to or greater than the amount by weight of non-aqueous solvent. Also provided are methods of using the nanodispersion formulations, as well as kits that include the nanodispersion formulations.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following sections, the taxane nanodispersion formulations and taxane diluted solutions prepared therefrom, as well as methods using the same, are described in greater detail, as well as methods for preparing the nanodispersion formulations and diluted solutions, as well as kits that may include the formulations.

Aspects of the invention include taxane nanodispersion formulations. In some instances, the nanodispersion formulations are non-aqueous liquid, ethanol-free compositions that, upon combination with an aqueous medium, produce a taxane diluted solution. The non-aqueous, ethanol-free taxane liquid nanodispersion formulations of embodiments of the invention comprise a taxane, an oil, a non-ionic surfactant, a non-aqueous solvent, and an organic acid component, wherein the organic acid component is soluble in the non-aqueous solvent and the amount by weight of non-ionic surfactant is equal to or greater than the amount by weight of non-aqueous solvent. In certain embodiments, the non-aqueous, ethanol-free taxane liquid nanodispersion formulations of embodiments of the invention consist essentially of a taxane, an oil, a non-ionic surfactant, a non-aqueous solvent, and an organic acid component, wherein the organic acid component is soluble in the non-aqueous solvent and the amount by weight of non-ionic surfactant is equal to or greater than the amount by weight of non-aqueous solvent.

As used herein, the term "nanodispersion" refers a substantially clear (i.e., transparent) solution comprising nanosized particles. In some instances, the particle size ranges from about 3 to about 70 nm, from about 5 to about 50 nm, from about 7 to about 30 nm, or from about 8 to about 15 nm.

Taxanes of interest are diterpene compounds. In some instances, taxanes are compounds described by the formula:

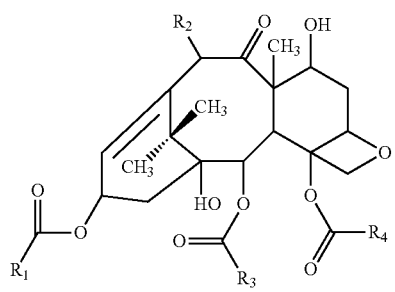

where: $R_1 =$

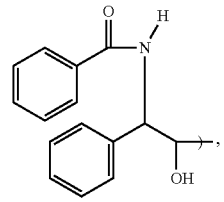

, alkyl of 1 to 6 carbons or phenyl $R_2 =$ , —OH, or $CH_3(CH_2)_x$ ... O— where X = 0-6

$R_3$ = alkyl of 1 to 6 carbons or phenyl; and
$R_4$ = alkyl of 1 to 6 carbons or phenyl.

Of interest are anhydrous taxanes as well as hydrates thereof, e.g., mono, di, tri, tetra and penta hydrates, etc. In certain embodiments, the taxane is paclitaxel or docetaxel, including anhydrous or a hydrate thereof, e.g., anyhydrous docetaxel, docetaxel trihydrate, paclitaxel trihydrate, etc., may be employed in the formulations. Taxanes of interest also include, but are not limited to: 7-epitaxol, 7-acetyl taxol, 10-desacetyl-taxol, 10-desacetyl-7-epitaxol, 7-xylosyltaxol, 10-desacetyl-7-glutaryltaxol, 7-N,N-dimethylglycyltaxol, 7-L-alanyltaxol, SB-T-1011, etc. The taxane may be present as a free base or salt.

Taxane nanodispersion formulations include an effective amount of a taxane. By effective amount is meant a dosage sufficient to provide the desired result, e.g., inhibition of cellular proliferation. The effective amount of taxane may vary depending on the particular taxane employed, and in certain embodiments ranges from 0.05 to 5% by weight, such as 0.5 to 5% by weight and including 0.3 to 3% by weight. In certain embodiments, the nanodispersion formulations include an effective amount of paclitaxel or paclitaxel trihydrate. In certain embodiments, paclitaxel or paclitaxel trihydrate is present in the nanodispersion formulation in an amount ranging from 0.05 to 5.0% w/w, such as 0.5 to 5.0% w/w, and including 0.3 to 3.0% w/w, where in some instances the amount ranges from 0.3 to 5.0% w/w, such as 0.3 to 3.0% w/w, e.g., 0.4 to 2.5% w/w, e.g., 0.5 to 2.0% w/w, and including 1.0 to 1.5% w/w. In certain embodiments, the nanodispersion formulations include an effective amount of docetaxel or docetaxel trihydrate. In certain embodiments, anhydrous docetaxel or docetaxel trihydrate is present in the nanodispersion formulation in an amount ranging from about 0.1 to about 5 wt %, or from about 0.5 to about 5 wt %, or from about 0.5 to about 3 wt %, or from about 1 to about 3 wt %, or is about 2 wt %. The concentration of the taxane in the formulations may vary, and is in some embodiments, about 30 mg/ml or less, about 25 mg/ml or less, about 20 mg/ml or less, about 10 mg/ml or less, about 1 mg/ml or less, or ranges from about 0.05 to about 20 mg/ml, from about 0.5 to about 20 mg/ml, from about 1 to about 20 mg/ml, or from about 5 to about 20 mg/ml.

As used herein, the term "non-aqueous" is intended to refer to formulations having a water content about 3% by weight or less. The water content may come from any one or more of the components in the formulation, such as the organic acid component or from the water associated with docetaxel trihydrate, when used. In some embodiments, the formulations comprise less than about 3% water by weight, or less than about 2.5% water by weight, or less than about 2% water by weight, or less than about 1.5% water by weight, or less than about 1% water by weight, or less than about 0.5% water by weight, or less than about 0.1% water by weight, or less than about 0.01% water by weight, or than about 0.005% water by weight.

Also present in the nanodispersion formulations is an oil component made up of one or more oils. Without wishing to be bound by any one theory, it is contemplated that the inclusion of the oil in the nanodispersion formulation helps stabilize the diluted solution. Oils of interest are physiologically acceptable and include, but are not limited to: simple lipids, derived lipids, complex lipids that are derived from vegetable oil and fat, animal oil and fat, or mixtures thereof, where the oils may be naturally occurring or synthetic.

In certain embodiments, the oil includes, but is not limited to vegetable oil such as soybean oil, olive oil, sesame oil, castor oil, corn oil, peanut oil, safflower oil, grape seed oil and eucalyptus oil, medium-chain fatty acid esters, low-chain fatty acid esters, triglycerides, and the like. Animal oils and fat of interest include, but are not limited to, cod-liver oil, seal oil, sardine oil, docosahexiaenoic acid, and eicosapentaenoic acid. One or a combination of more than one of these types of oils can be used. For example, some embodiments of the subject formulations include soybean oil, olive oil, sesame oil, or combinations thereof. Other embodiments include soybean oil, olive oil, or combinations thereof. Highly refined oils and fats are employed in certain embodiments. In some embodiments, the oil is soybean oil. In some embodiments, the oil is a medium chain triglyceride (i.e., a medium chain fatty acid ester). In some embodiments, the oil is not a medium chain triglyceride (i.e., a medium chain fatty acid ester).

Oils to be used in the formulations disclosed herein may also include tocopherols. Tocopherols are a family of natural and synthetic compounds, also known by the generic names tocols or Vitamin E. α-Tocopherol is the most abundant and active form of this class of compounds and it has the following chemical structure:

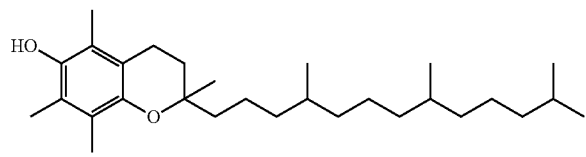 [SMILES: Cc1c(C)c2c(c(C)c1O)CCC(C)(CCCC(C)CCCC(C)CCCC(C)C)O2]

Other members of this class include α-, β-, γ-, and δ-tocotrienols, and α-tocopherol derivatives such as tocopherol acetate, phosphate, succinate, nitotinate and linoleate. Any convenient tocopherol may be present, as desired, including the specific tocopherols listed above.

Oils of interest also include polyol esters of medium chain fatty acids. The term "polyol esters of medium chain fatty acids" is intended to include esters and mixed esters of glycerol, propylene glycol or other open chain polyols such as polyethylene glycol, reacted with medium chain fatty acids, e.g., where the acid has a chain length between 6 and 12 carbon atoms. In some instances, the polyol esters of medium chain fatty acids are triglycerides or diglycerides of the $C_8$-$C_{10}$ fatty acids, e.g., as may be commercially available from the fractionation of coconut oil. Commercially available products of this description are sold under the trade names "NEOBEE®", "ODO®", "Panacet®", "Miglyol®" and "Captex® 300" and have a majority of $C_8$ fatty acid (caprylic) triglyceride and $C_{10}$ fatty acid (capric) triglyceride with minor levels of $C_6$ and $C_{14}$ fatty acid triglycerides. In some embodiments, the oil is NEOBEE®.

In certain embodiments, the oil is selected from the group consisting of synthetic oils, vegetable oils, tocopherols and combinations thereof. In other embodiments, the oil is selected from the group consisting of soybean oil, olive oil, sesame oil, corn oil, a medium chain triglyceride, a tocopherol or derivative thereof and combinations thereof.

In certain embodiments, the oil is about 20 wt % or less of the formulation. In some instances, the amount of oil in the nanodispersion formulation ranges from about 0.5 to about 20 wt %, or from about 1 to about 20 wt %, or from about 1 to about 10 wt %. In certain embodiments, the oil is present in an amount ranging from about 1 to about 5 wt %. In other embodiments, the oil is present in an amount ranging from about 1 to about 3 wt %, or about 2 wt %. In certain embodiments, the amount of oil in the nanodispersion formulation is calculated based on the amount of docetaxel in the formulation. For example, in some embodiments, when the amount of oil greatly exceeds the amount of docetaxel (w/w), the particle size can become larger, which typically results in the formulation becoming cloudy. Accordingly, in some embodiments, the amount of oil is less than about three times the amount of taxane (w/w), or equal to or less than about 2.5 times the amount of taxane (w/w), or equal to or less than about 2 times the amount of taxane (w/w), or equal to or less than about 1.5 times the amount of taxane (w/w), or is about equal to the amount of taxane (w/w), or is about half of the amount of taxane (w/w).

Also present in the nanodispersion formulations is a non-ionic surfactant, which may include one or more non-ionic surfactants. Surfactants of interest include any type of non-ionic surfactant that can be used for pharmaceutical formulations. Non-ionic surfactants of interest include, but are not limited to, polyoxyalkylene copolymer, and sorbitan fatty acid esters. In some embodiments, the sorbitan fatty acid ester is a polyoxyethylene sorbitan fatty acid ester (e.g., polyoxyethylene sorbitan tristearate (Tween® 65); polyoxyethylene sorbitan trioleate (Tween® 85); polyethylene glycol 400 monostearate; polysorbate 60; (Tween® 60); polyoxyethylene monostearate (Myrj® 49); polysorbate 80 (Tween® 80); polysorbate 40 (Tween® 40); and polysorbate 20 (Tween 20)) or sorbitan fatty acid esters (e.g., sorbitan trioleate (Span® 85); sorbitan tristearate (Span® 65); sorbitan sesquioleate (Arlacel® 83); glyceryl monostearate; sorbitan monooleate (Span® 80); sorbitan monostearate (Span® 60); sorbitan monopalmitate (Span® 40); and sorbitan monolaurate (Span® 20)). In some embodiments, the non-ionic surfactant is polysorbate 80. In some embodiments, the polysorbate 80 is refined grade.

The amount of non-ionic surfactant in the nanodispersion formulation may vary. In some instances, the amount of non-ionic surfactant in the nanodispersion formulation is 40 wt % or more. In some instances, the non-ionic surfactant is present in an amount ranging from about 40 to about 75 wt %, or from about 50 to about 65 wt %, or from about 50 to about 60 wt %, or from about 50 to about 57 wt %, or from about 57 to about 65 wt %. The combination ratio by weight of the oil and the surfactant in the subject nanodispersion formulations may vary, and is in some instances about 1/100, or 1/50, or 1/40, or 1/30, or 1/20, or 1/10, or 1/8, or 1/6, or 1/4, or 1/2, or 1/1.

The nanodispersion formulations of the invention further include a non-aqueous solvent, which may include one or more non-aqueous solvents. Non-aqueous solvents of interest include, but are not limited to, propylene glycol, polypropylene glycol, polyethylene glycol (such as PEG 300, PEG 400, PEG 600, PEG 800, PEG 1000, etc., where in certain embodiments polyethylene glycols, when employed, have an average molecular weight of 1000 or less), glycerin, triacetin, dimethyl isosorbide, glycofurol, propylene carbonate, dimethyl acetamide or a mixture thereof. In some embodiments, the non-aqueous solvent is polyethylene glycol. In some embodiments, the non-aqueous solvent is polyethylene glycol 400. In some embodiments, the polyethylene glycol has a melting point of less than 0° C. In some embodiments, the non-aqueous solvent is polyethylene glycol 300.

The non-aqueous solvent may be present in varying amounts, and in some instances is present in an amount ranging from about 20 to about 60 wt %, or from about 35 to about 45 wt %, including amounts ranging from about 35 to about 40 wt %, or from about 40 to about 45 wt %.

In the present formulations, the amount of non-ionic surfactant (w/w) should be about equal to or greater than the amount of non-aqueous solvent (w/w) in the formulation, or greater than about 95% of the amount of non-aqueous solvent (w/w), or in other words, the ratio by weight of the non-ionic surfactant and the non-aqueous solvent is 0.95 or more. As shown in the Examples, when used in such amounts, the stability of the formulation is enhanced.

In the present nanodispersions, the combination ratio by weight of the oil and the non-aqueous solvent in the nanodispersion formulations may vary, and in some instances is 1/100, or 1/50, or 1/40, or 1/30, or 1/20, or 1/10, or 1/7, or 1/5, or 1/3, or 1/1.

The nanodispersion formulation further comprises an organic acid component. An organic acid component may include an organic acid and/or an organic acid buffer (i.e., an organic acid and its conjugate base (or salt thereof)). Therefore, in some instances, the organic acid buffer comprises an organic acid and a salt of its conjugate base. Organic acids of interest upon which the organic acid component may be based include those which are soluble in the non-aqueous solvent (in the amount used). Specific examples include lactic acid, succinic acid, malic acid, tartaric acid and acetic acid.

In some instances, the organic acid component is a lactic acid/sodium lactate component, such that the component includes both lactic acid and sodium lactate. As organic acid can be hydroscopic and may contain a small or trace amount of water, the lactic acid and/or sodium lactate can be commercially available or substantially dehydrated prior to use. In some instances, the lactic acid/sodium lactate component is present in an amount ranging from about 0.3 to 3 wt %, or from about 0.3 to about 2 wt %, or from about 0.3 to about 1.5 wt %, or from about 0.5 to about 1.5 wt %, or from about 0.8 to about 1.2 wt %, or from about 0.8 to about 1 wt %, or about 1 wt %.

In other instances, the organic acid component, e.g., lactic acid or acetic acid, does not contain any significant amount of its conjugate base (or salt thereof). In addition, in some embodiments, the nanodispersion formulations disclosed herein do not contain a buffer or a mineral acid. In some embodiments, the organic acid component is lactic acid. The lactic acid can be D- or L-lactic acid, or a mixture thereof. The organic acid may be present in varying amounts, and in some instances is present in an amount ranging from about 0.3 to about 3 wt %, or from about 0.3 to about 1 wt %, or from about 0.3 to about 0.6 wt %, or from about 0.4 to about 0.5 wt %, or from about 0.5 to about 1 wt %, or from about 0.7 to about 1 wt %, or about 0.8 wt %.

In some embodiments, the present disclosure provides for a non-aqueous, ethanol-free docetaxel liquid nanodispersion formulation comprising: docetaxel, soybean oil in an amount ranging from about 1 to about 5 wt %, polysorbate 80 in an amount ranging from about 50 to about 60 wt %, polyethylene glycol in an amount ranging from about 35 to about 45 wt %, and lactic acid or lactic acid buffer in an amount ranging from 0.3 to 1 wt %, wherein the amount by weight of non-ionic surfactant is equal to or greater than the amount by weight of non-aqueous solvent.

In another embodiment, the present disclosure provides for a non-aqueous, ethanol-free docetaxel liquid nanodispersion formulation comprising: docetaxel, a medium chain triglyceride in an amount ranging from about 1 to about 5 wt %, polysorbate 80 in an amount ranging from about 50 to about 60 wt %, polyethylene glycol in an amount ranging from about 35 to about 45 wt %, and lactic acid or lactic acid buffer in an amount ranging from 0.3 to 1 wt %, wherein the amount by weight of non-ionic surfactant is equal to or greater than the amount by weight of non-aqueous solvent.

The nanodispersion formulation as described above typically has a pH of less than about 4, or less than about 3.5, or less than about 3.4, or less than about 3.3, or less than about 3.25, or less than about 3.2, or less than about 3.1, or from about 3.0 to about 3.1.

Methods of Preparing Taxane Nanodispersion Formulations

Nanodispersion formulations may be prepared according to any convenient protocol. As such, the components of the desired nanodispersion may be combined under conditions sufficient to produce the desired nanodispersion. Accordingly, an amount of taxane, oil, non-ionic surfactant, non-aqueous solvent, and organic acid component, wherein the organic acid component is soluble in the non-aqueous solvent and the amount by weight of non-ionic surfactant is equal to or greater than the amount by weight of non-aqueous solvent, may be combined under conditions sufficient to produce a nanodispersion. The components may be combined in any convenient order. The components may be combined at any convenient temperature, e.g., room temperature or elevated temperatures, such as temperatures ranging from 30 to 95° C., or 50 to 60° C., or 70 to 80° C. Certain of the components may be combined with each other, and then combined together, or all of the components may be combined at substantially the same time. Combination may include various manners of agitation or mixing, e.g., stirring, sonication, etc., in order to produce the nanodispersion. Depending on the particular preparation method, an aqueous solvent, e.g., water, etc. may or may not be employed during preparation of the nanodispersion compositions.

In one embodiment, a nanodispersion is prepared without an aqueous solvent. In these embodiments, the desired amounts of components of the nanodispersion, e.g., taxane, oil, non-ionic surfactant, non-aqueous solvent, and organic acid component are combined. Combination may include various manners of agitation, e.g., stirring, sonication, etc., in order to produce the nanodispersion. Where desired, heat may be employed to facilitate mixing, although, in some embodiments, the combining is performed at ambient temperature. In certain embodiments, the nanodispersion is clear. By clear is meant that the nanodispersion is a translucent, if not transparent liquid, i.e., the liquid is pellucid.

In some instances, the nanodispersion preparation protocol includes use of an aqueous solvent, e.g., pure water. In these instances, an aqueous formulation is prepared, which includes taxane, oil, non-ionic surfactant, non-aqueous solvent, organic acid component and an aqueous solvent, e.g., water, etc. In certain embodiments, the aqueous formulation composition is clear. By clear is meant that the nanodispersion is a translucent, if not transparent liquid, i.e., the liquid is pellucid. As such, the initial preparation is not cloudy. In some instances, the particle size of the initial composition ranges from about 3 to about 70 nm, such as about 5 to about 50 nm and including about 7 to about 30 nm, such as about 8 to about 15 nm. Of interest in certain embodiments are initial compositions that are clear (e.g., as described above) and have a particle size of about 70 nm or less, such as about 50 nm or less, including about 30 nm or less, including about 25 nm or less, about 20 nm or less and about 15 nm or less. In these embodiments, as a final step, water may be removed from the composition to produce a final, non-aqueous nanodispersion. Removal of water may be accomplished using any convenient protocol, e.g., via a combination of pressure and/or temperature modulation, such as heating.

The preparation methods can be carried out at certain temperature such as temperatures ranging from about 30° C. to about 95° C., about 50° C. to about 60° C., about 60° C. to about 70° C., or about 70° C. to about 80° C. Specific examples are provided in the Experimental section, below.

In some embodiments, the method for making the ethanol-free taxane nanodispersion formulation as disclosed herein does not comprise the addition of water and/or ethanol, followed by removal thereof. Accordingly, since the non-aqueous, ethanol-free taxane nanodispersion formulation has not been contacted with either water or ethanol during the formulation process, it is substantially free of water (i.e. less than about 3%) and free of ethanol. In some embodiments, the formulation is essentially free of water (i.e, less than about 1%). In addition, in certain embodiments, the formulations do not have any detectable amount of ethanol. This results in a formulation which is stable and can be suitable for subjects having an adverse reaction to ethanol. In some embodiments, the formulations do not contain activated carbon.

Where desired, an amount of the nanodispersion may be loaded into an individual dosage container, e.g., vial, which holds the nanodispersion and keeps it sterile during shipping, storage, and handling. Before or during the loading stage, the nanodispersion can be passed through a sub-micron sterilizing filter, e.g., a 0.2μ hydrophilic filter) which has a sufficiently small pore size to remove any bacteria or viruses. The sterilizing filters of interest include, but are not limited to hydrophilic filters. In some embodiments, the filter could be a CA (Cellulose Acetate) membrane filter, PTFE (Polytetrafluoroethylene) membrane filter, PVDF (Polyvinylidene fluoride or polyvinylidene difluoride) membrane filter or PES (Polyethersulfone) membrane filter.

As used herein, the term "vial" refers to any container that is used to hold the nanodispersion formulation. Many pharmaceutical vials are made of clear glass, which allows several advantages, including visual inspection of the enclosed drug (to ensure that it is still in a clean, non-caramelized, non-collapsed form, when it is ready for use) and of the container itself (to ensure that it does not have a hairline crack in one of the walls, which could jeopardize or destroy sterility of the enclosed drug). Various types of pharmaceutical vials are known. Single-chamber vials can be sealed with rubber or plastic plugs that will allow a hypodermic needle to be pushed through the rubber seal. Examples include any hydrolytically stable glass, such as a borosilicate Type I or soda-lime-silica Type II glass vial, having a suitable stopper (e.g., Teflon coating). Alternately, a single-chamber vial can be made of a brittle and easily breakable material, inside a sealed bag that can contain an aqueous solution (such as physiological saline or a dextrose solution, in an intravenous infusion bag); if this type of vial is broken, it will release its contents into the still-sealed bag, for mixing. In yet other embodiments, two-chamber vials or analogous structures, e.g., as described in Published United States Application Publication No. 2003/0099674 and U.S. Pat. No. 4,781,354 may be employed. Other methods for preparing the taxane formulations disclosed herein can be found in Published United States Application Publication No. 2011/0269829, the entirety of which is incorporated herein by reference.

Where desired, the nanodispersion formulation may be stored for a period of time prior to combination with the aqueous medium. This storage time of the nanodispersion may vary, where storage times may be 1 year or more, such as 2 years or more, including 3 years or more. While the storage conditions may vary, in certain instances the storage conditions are characterized by a temperature ranging from about 5 to 60° C., e.g., 5° C., such as about 8 to 40° C., e.g., about 25° C. The activity of the taxane active agent is substantially preserved during the storage period, such that the nanodispersion formulations are storage stable. As such, the activity of the taxane active agent in the infusion solution following storage is substantially the same as that in the nanodispersion prior to being dried, where the magnitude of any difference in activity between the nanodispersion and diluted solution may be about 15% or less, such as about 10% or less, including about 5% or less, e.g., as can be measured by HPLC.

As shown in the Examples, the nanodispersion formulation according the present disclosure is stable for at least 6 months (see Examples 3 and 6) at 40° C. The stability of the present nanodispersion formulations can be determined by methods known in the art, such as by measuring the recovery rate for the taxane (e.g., docetaxel) peak by HPLC. In some embodiments, the nanodispersion formulation exhibits a taxane (e.g., docetaxel) recovery rate of more than about 95% after 6 months at about 40° C., or about 96% or more, or more than about 97% or more, or more than about 98% or more, or about 99% or more. The recovery rate is calculated based on the measured amount of docetaxel in the formulation, which is not necessarily the amount of docetaxel added to the formulation (thus eliminating any potential error from an impurity in the docetaxel).

Taxane Diluted Solutions and Methods of Use

Following preparation of the nanodispersion formulation, e.g., as described above, at the time of desired administration to a subject, a dosage amount of the nanodispersion may be combined with an aqueous medium to prepare an diluted solution that is suitable for use. The dosage amount of the nanodispersion formulation may be combined with any suitable aqueous medium, where aqueous mediums of interest include, but are not limited to: deionized water, USP water for injection (WFI), salines, transfusion solutions, physiological solutions, etc. In some embodiments, the aqueous medium comprises an aqueous 0.9% sodium chloride solution or an aqueous 5% dextrose or glucose solution. The liquids to nanodispersion (high viscous liquid) ratio employed during preparation of the diluted solution may vary, and in certain embodiments ranges from about 0.5 to about 300, such as about 1 to about 100, about 2 to about 50 or about 2 to about 20, and including about 2 to about 10. In some instances, the dosage amount of nanodispersion formulation that is combined with the aqueous medium ranges from about 100 to about 1200 g, such as about 300 to about 600 g and the amount of aqueous medium that is combined with the dosage amount ranges from about 100 to about 1200 ml, such as about 250 to about 600 ml.

The diluted solution prepared from the nanodispersion formulations are liquid preparations that are a suspension of small particles (i.e., globules) of one liquid in a second liquid with which the first liquid will not mix. The water present in the taxane diluted solutions may be any convenient water, including deionized water, USP water for injection (WFI), etc.

The combination protocol may vary, where agitation may be employed, e.g., by stirring, by kneading a bag that includes both the nanodispersion and the aqueous medium, etc.

The diluted solutions include a taxane, an oil component, a non-ionic surfactant component, a non-aqueous solvent component and an aqueous medium. In certain embodiments, the diluted solutions are clear. By clear is meant that the diluted solution is a translucent, if not transparent liquid, i.e., the liquid is pellucid. As such, the diluted solution is not cloudy, e.g., as a suspension may appear. Further details regarding the diluted solutions that may be prepared from the taxane nanodispersion precursors are provided below. In some instances, the particle size of the final diluted solution ranges from about 3 to about 70 nm, such as about 5 to about 50 nm and including about 7 to about 30 nm, such as about 8 to about 15 nm. Of interest in certain embodiments are diluted solutions that are clear (e.g., as described above) and have a particle size of about 70 nm or less, such as about 50 nm or less, including about 30 nm or less, including about 25 nm or less, about 20 nm or less and about 15 nm or less. In some instances, any difference in particle size between the nanodispersion and diluted solutions is minimal, such that the particle sizes in the nanodispersion and diluted solutions are substantially the same. In some instances, any difference in particle size between the nanodispersion and diluted solutions is about 30 nm or less, such as about 20 nm or less, about 15 nm or less, about 10 nm or less, or about 5 nm or less. Without wishing to be bound by any one theory, it is contemplated that the inclusion of the oil in the nanodispersion formulations helps stabilize the diluted solution.

The diluted solutions have a physiologically acceptable pH. In certain embodiments, the pH of the diluted solutions ranges from about 2.5 to about 8, such as from about 3 to about 7, including from about 3.5 to about 6. The diluted solutions are substantially clear (i.e., transparent) formulations. The concentration of the taxane in the diluted solutions may vary, ranging in some embodiments from about 0.05 to about 10 mg/ml, such as about 0.2 to about 3 mg/ml.

Methods of using the diluted solutions include administering an effective amount of the diluted solutions to a subject in order to treat the subject for a target condition of interest. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated, such as pain. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the diluted solutions disclosed herein can be parenterally administered to a subject. By "parenteral administration" is meant administration by a protocol that delivers a quantity of the diluted solutions to the subject, e.g., a patient suffering from a cellular proliferative disease, by a route other than the digestive tract. Examples of parenteral administration include, but are not limited to, intramuscular injection, intravenous injection, and the like. In certain embodiments, parenteral administration is by injection using an injection delivery device.

The amount of diluted solution that is administered to the subject may vary depending on a number of factors, such as patient specifics, nature of condition, nature of taxane active agent, etc. In certain embodiments, the volume of diluted solution that is administered to a subject may range from about 100 to about 1000 ml, such as about 200 to about 600 ml. The time period over which this volume is administered may vary, ranging from about 0.5 to about 6 hr, such as from about 1 to about 3 hours. Dosages administered to a subject during a given procedure may also vary, ranging in some instances from about 20 to about 500 $mg/m^2$, such as from about 50 to about 300 $mg/m^2$.

Accordingly, provided herein are methods of administering an non-aqueous, ethanol-free taxane liquid nanodispersion formulation to a subject, the method comprising: (a) combining the non-aqueous, ethanol-free taxane liquid nanodispersion formulation according to the present disclosure with an aqueous medium to provide a diluted solution; and (b) administering the diluted solution to the subject.

In some embodiments, the method of using the nanodispersion formulation disclosed herein comprises the steps of: (a) aseptically withdrawing the desired amount of the nanodispersion formulation (such as a formulation comprising about 20 mg taxane/mL) with a calibrated syringe, (b) injecting said formulation into a 250 mL infusion bag or bottle of either 0.9% sodium chloride solution or 5% dextrose solution to provide a diluted solution having a final taxane concentration of from about 0.3 mg/mL to about 0.74 mg/mL, and (c) administering said diluted solution to a patient. If a dose greater than 200 mg of taxane is required, one may use a larger volume of the infusion vehicle so that a concentration of 0.74 mg/mL taxane is not exceeded.

In certain embodiments, the subject methods include a diagnostic step. Individuals may be diagnosed as being in need of the subject methods using any convenient protocol. In addition, individuals may be known to be in need of the subject methods, e.g., they are suffering from a target disease condition (e.g., cellular proliferative disease, prior to practicing the subject methods. Diagnosis or assessment of target condition can be performed using any convenient diagnostic protocol.

Methods of the invention may further include assessing the efficacy of the treatment protocol that includes administration of the taxane diluted solution. Assessing the efficacy of treatment may be performed using any convenient protocol.

Taxane diluted solutions of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

In determining whether to administer the diluted solution to a particular given subject, care will be taken to ensure that the formulation is not contraindicated for that subject. As such, symptoms of the subject may be assessed to ensure that administration of the diluted solution will not have adverse effects that outweigh any benefit that the diluted solution may provide.

Utility

The subject formulations, diluted solutions and/or methods find use in a variety of applications, including the treatment of subjects suffering from cellular proliferative disease conditions. Cellular proliferative diseases that may be treated with formulations of the invention include, but are not limited to: carcinomas, myelomas, neuroblastomas, or sarcomas, of the brain, breast, lung, colon, prostate or ovaries, as well as leukemias or lymphomas. Specific disease conditions of interest include, but are not limited to, human ovarian cancer, breast cancer, malignant lymphoma, lung cancer, melanoma, and Kaposi's sarcoma.

Kits

Also provided are kits that find use in practicing the subject methods, as described above. For example, kits for practicing the subject methods may include a quantity of the nanodispersion formulation, present in unit dosages, e.g., vials, or a multi-dosage format. As such, in certain embodiments, the kits may include one or more unit dosages (e.g., vials) of the nanodispersion formulation. The term "unit dosage", as used herein, refers to physically discrete units suitable as unitary dosages for human and animal subjects, each unit containing a predetermined quantity of the subject nanodispersion formulation calculated in an amount sufficient to produce the desired effect. The amount of the unit dosage of the subject formulation depends on various factors, such as the particular active agent employed, the effect to be achieved, and the pharmacodynamics associated with the active agent in the subject. In yet other embodiments, the kits may include a single multi-dosage amount of the formulation.

In certain embodiments, the kits may further include an amount of an aqueous medium suitable for use in production of the diluted solution. The aqueous medium may be any convenient aqueous medium, such as described above, present in any suitable container, e.g., an IV bag.

In some embodiments, the kits may include a syringe which is suitable to prepare the docetaxel diluted solution. A syringe with graduations is preferred to measure a certain amount of the docetaxel nanodispersion.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., one or more pieces of paper on which the information is printed, in the packaging of the kit, in a package insert, etc. The instructions may be present on a computer readable medium, e.g., diskette, CD, DVD, etc., on which the information has been recorded. The instructions may be present on a website, which may be used via the internet to access the information at a removed site. Other convenient means are possible and may be included in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Docetaxel Nanodispersion Formulations

Aspects of the invention include docetaxel nanodispersion formulations. In some instances, the nanodispersion formulations are non-aqueous, ethanol-free docetaxel liquid compositions that, upon combination with an aqueous medium, produce a docetaxel diluted solution. The non-aqueous liquid nanodispersion formulations of embodiments of the invention comprise docetaxel, an oil, a non-ionic surfactant, a non-aqueous solvent and an organic acid, wherein said organic acid is soluble in the non-aqueous solvent and is substantially free of any conjugate base. In certain embodiments, the non-aqueous liquid nanodispersion formulations of embodiments of the invention consists essentially of docetaxel, an oil, a non-ionic surfactant, a non-aqueous solvent and an organic acid, wherein said organic acid is soluble in the non-aqueous solvent and is substantially free of any conjugate base.

As used herein, the term "nanodispersion" refers a substantially clear (i.e., transparent) solution comprising nanosized particles. In some instances, the particle size ranges from about 3 to about 70 nm, from about 5 to about 50 nm, from about 7 to about 30 nm, or from about 8 to about 15 nm.

Anhydrous docetaxel as well as hydrates thereof, e.g., mono, di, tri, tetra and penta hydrates, etc, may be employed in the docetaxel nanodispersion formulations. In certain embodiments, the docetaxel is anhydrous docetaxel. In other embodiments, the docetaxel is docetaxel trihydrate.

Nanodispersion formulations include an effective amount of docetaxel. By effective amount is meant a dosage sufficient to provide the desired result, e.g., inhibition of cellular proliferation. The effective amount of docetaxel may range from about 0.1 to about 5 wt %, or from about 0.5 to about 5 wt % (weight percent), or from about 0.5 to about 3 wt %, or from about 1 to about 3 wt %, or is about 2 wt %. Therefore, in certain embodiments, anhydrous docetaxel or docetaxel trihydrate is present in the nanodispersion formulation in an amount ranging from about 0.1 to about 5 wt %, or from about 0.5 to about 5 wt %, or from about 0.5 to about 3 wt %, or from about 1 to about 3 wt %, or is about 2 wt %. The concentration of the taxane in the formulations may vary, and is in some embodiments, about 30 mg/ml or less, about 25 mg/ml or less, about 20 mg/ml or less, about 10 mg/ml or less, about 1 mg/ml or less, or ranges from about 0.05 to about 20 mg/ml, from about 0.5 to about 20 mg/ml, from about 1 to about 20 mg/ml, or from about 5 to about 20 mg/ml.

As used herein, the term "non-aqueous" is intended to refer to formulations having a water content about 3% by weight or less. The water content may come from any one or more of the components in the formulation, such as the organic acid component or from the water associated with docetaxel trihydrate, when used. In some embodiments, the formulations comprise less than about 3% water by weight, or less than about 2.5% water by weight, or less than about 2% water by weight, or less than about 1.5% water by weight, or less than about 1% water by weight, or less than about 0.5% water by weight, or less than about 0.1% water by weight, or less than about 0.01% water by weight, or than about 0.005% water by weight.

Also present in the nanodispersion formulations is an oil component made up of one or more oils. Without wishing to be bound by any one theory, it is contemplated that the inclusion of the oil in the nanodispersion formulations helps stabilize the diluted solution. Oils of interest are physiologically acceptable and include, but are not limited to: simple lipids, derived lipids, complex lipids that are derived from vegetable oil and fat, animal oil and fat, and mineral oil, or mixtures thereof, where the oils may be naturally occurring or synthetic.

In certain embodiments, the oil includes, but is not limited to vegetable oil such as soybean oil, olive oil, sesame oil, castor oil, corn oil, peanut oil, safflower oil, grape seed oil and eucalyptus oil, medium-chain fatty acid esters, low-chain fatty acid esters, triglycerides, and the like. Animal oils and fat of interest include, but are not limited to, cod-liver oil, seal oil, sardine oil, docosahexiaenoic acid, and eicosapentaenoic acid. One or a combination of more than one of these types of oils can be used. For example, some embodiments of the subject formulations include soybean oil, olive oil, sesame oil, or combinations thereof. Other embodiments include soybean oil, olive oil, or combinations thereof. Highly refined oils and fats can be employed in certain embodiments. In some embodiments, the oil is soybean oil.

Oils to be used in the formulations disclosed herein may also include polyol esters of medium chain fatty acids. The term "polyol esters of medium chain fatty acids" is intended to include esters and mixed esters of glycerol, propylene glycol or other open chain polyols such as polyethylene glycol, reacted with medium chain fatty acids, e.g., where the acid has a chain length between 6 and 12 carbon atoms. In some instances, the polyol esters of medium chain fatty acids are triglycerides or diglycerides of the $C_8$-$C_{10}$ fatty acids, e.g., as may be commercially available from the fractionation of coconut oil. Commercially available products of this description are sold under the trade names "NEOBEE®", "ODO® " "Panacet®", "Miglyol®" and "Captex® 300" and have a majority of $C_8$ fatty acid (caprylic) triglyceride and $C_{10}$ fatty acid (capric) triglyceride with minor levels of $C_6$ and $C_{14}$ fatty acid triglycerides. In some embodiments, the oil is NEOBEE®.

In certain embodiments, the oil is about 20 wt % or less of the formulation. In some instances, the amount of oil in the nanodispersion formulation ranges from about 0.5 to about 20 wt %, or from about 1 to about 20 wt %, or from about 1 to about 10 wt %. In certain embodiments, the oil is present in an amount ranging from about 1 to about 5 wt %. In other embodiments, the oil is present in an amount ranging from about 1 to about 3 wt %, or about 2 wt %. In certain embodiments, the amount of oil in the nanodispersion formulation is calculated based on the amount of docetaxel in the formulation. For example, in some embodiments, when the amount of oil greatly exceeds the amount of docetaxel (w/w), the particle size can become larger, which typically results in the formulation becoming cloudy. Accordingly, in some embodiments, the amount of oil is less than about three times the amount of docetaxel (w/w), or equal to or less than about 2.5 times the amount of docetaxel (w/w), or equal to or less than about 2 times the amount of docetaxel (w/w), or equal to or less than about 1.5 time the amount of docetaxel (w/w), or is about equal to the amount of docetaxel (w/w), or is about half of the amount of docetaxel (w/w).

Also present in the nanodispersion formulations is a non-ionic surfactant, which may include one or more non-ionic surfactants. Surfactants of interest include any type of non-ionic surfactant that can be used for pharmaceutical formulations. Non-ionic surfactants of interest include, but are not limited to, polyoxyalkylene copolymer, and sorbitan fatty acid esters. In some embodiments, the sorbitan fatty acid ester is a polyoxyethylene sorbitan fatty acid ester (e.g., polyoxyethylene sorbitan tristearate (Tween® 65); polyoxyethylene sorbitan trioleate (Tween® 85); polyethylene glycol 400 monostearate; polysorbate 60; (Tween® 60); polyoxyethylene monostearate (Myrj® 49); polysorbate 80 (Tween® 80); polysorbate 40 (Tween® 40); and polysorbate 20 (Tween 20)) or sorbitan fatty acid esters (e.g., sorbitan trioleate (Span® 85); sorbitan tristearate (Span® 65); sorbitan sesquioleate (Arlacel® 83); glyceryl monostearate; sorbitan monooleate (Span® 80); sorbitan monostearate (Span® 60); sorbitan monopalmitate (Span® 40); and sorbitan monolaurate (Span® 20)). In some embodiments, the non-ionic surfactant is polysorbate 80. In some embodiments, the polysorbate 80 is refined grade.

The amount of non-ionic surfactant in the nanodispersion formulation may vary. In some instances, the amount of non-ionic surfactant in the nanodispersion formulation is about 40 wt % or more. In some instances, the non-ionic surfactant is present in an amount ranging from about 40 to about 75 wt %, or from about 50 to about 65 wt %, or from about 50 to about 60 wt %, or from about 50 to about 57 wt %, or from about 57 to about 65 wt %. The combination ratio by weight of the oil and the surfactant in the subject nanodispersion formulations may vary, and is in some instances about 1/100, or about 1/50, or about 1/40, or about 1/30, or about 1/20, or about 1/10, or about 1/8, or about 1/6, or about 1/4, or about 1/2, or about 1/1.

In some instances, nanodispersion formulations of the invention further include a non-aqueous solvent, which may include one or more non-aqueous solvents. Non-aqueous solvents of interest include, but are not limited to, propylene glycol, polypropylene glycol, polyethylene glycol (such as PEG 300, PEG 400, PEG 600, PEG 800, PEG 1000, etc., where in certain embodiments polyethylene glycols, when employed, have an average molecular weight of 1000 or less), glycerin, triacetin, dimethyl isosorbide, glycofurol, propylene carbonate, dimethyl acetamide or a mixture thereof. In some embodiments, the non-aqueous solvent is polyethylene glycol. In some embodiments, the non-aqueous solvent is polyethylene glycol 400. In some embodiments, the polyethylene glycol has a melting point of less than 0° C. In some embodiments, the non-aqueous solvent is polyethylene glycol 300.

The non-aqueous solvent may be present in varying amounts, and in some instances is present in an amount ranging from about 20 to about 60 wt %, or from about 35 to about 45 wt %, including amounts ranging from about 35 to about 40 wt %, or from about 40 to about 45 wt %. The combination ratio by weight of the oil and the non-aqueous solvent in the nanodispersion formulations may vary, and in some instances is about 1/100, or about 1/50, or about 1/40, or about 1/30, or about 1/20, or about 1/10, or about 1/7, or about 1/5, or about 1/3, or about 1/1.

In some instances, the amount of non-aqueous solvent is determined based on the amount of non-ionic surfactant in the formulation. In such cases, the amount of non-ionic surfactant (w/w) should be about equal to or greater than the amount of non-aqueous solvent (w/w) in the formulation, or greater than about 95% of the amount of non-aqueous solvent (w/w), or in other words, the ratio by weight of the non-ionic surfactant and the non-aqueous solvent is about 0.95 or more. As is shown in the Examples, when used in such amounts, the stability of the formulation is enhanced.

The nanodispersion formulations disclosed herein further comprise an organic acid component. The organic acid as used herein is soluble in the non-aqueous, ethanol-free formulation (in the amount used) and does not contain any significant amount of (i.e., is substantially-free of) its conjugate base (or salt thereof). In some embodiments, the organic acid contains less than about 5% of its conjugate base (or salt thereof), or less than about 4%, or less than about 3%, or less than about 2%, or less than about 1%, or less than about 0.5%, or less than about 0.1%, or less than about 0.05%, or less than about 0.01%. Organic acids of interest upon which the organic acid component may be based include lactic acid, succinic acid, malic acid, tartaric acid and acetic acid. In some embodiments, the nanodispersion formulations disclosed herein do not contain a buffer or a mineral acid. In some embodiments, the organic acid component is lactic acid. The lactic acid can be D- or L-lactic acid, or a mixture thereof.

The organic acid may be present in varying amounts, and in some instances is present in an amount ranging from about 0.3 to about 3 wt %, or from about 0.3 to about 1 wt %, or from about 0.3 to about 0.6 wt %, or from about 0.4 to about 0.5 wt %, or from about 0.5 to about 1 wt %, or from about 0.7 to about 1 wt %, or about 0.8 wt %.

In some embodiments, the present disclosure provides for a non-aqueous, ethanol-free docetaxel liquid nanodispersion formulation comprising: docetaxel, soybean oil in an amount ranging from about 1 to about 5 wt %, polysorbate 80 in an amount ranging from about 50 to about 60 wt %, polyethylene glycol in an amount ranging from about 35 to about 45 wt %, and lactic acid in an amount ranging from about 0.3 to about 1% w/w and wherein said lactic acid is substantially lactate-free.

In another embodiment, the present disclosure provides for a non-aqueous, ethanol-free docetaxel liquid nanodispersion formulation comprising: docetaxel, a medium chain triglyceride in an amount ranging from about 1 to about 5 wt %, polysorbate 80 in an amount ranging from about 50 to about 60 wt %, polyethylene glycol in an amount ranging from about 35 to about 45 wt %, and lactic acid in an amount ranging from about 0.3 to about 1% w/w and wherein said lactic acid is substantially lactate-free.

The nanodispersion formulation typically has a pH of less than about 3.5, or less than about 3.4, or less than about 3.3, or less than about 3.25, or less than about 3.2, or less than about 3.1, or from about 3.0 to about 3.1.

Methods of Preparing Docetaxel Nanodispersion Formulations

Nanodispersion formulations may be prepared according to any convenient protocol. As such, the components of the desired nanodispersion may be combined under conditions sufficient to produce the desired nanodispersion. Accordingly, an amount of docetaxel, an oil, a non-ionic surfactant, a non-aqueous solvent and an organic acid, wherein said organic acid is soluble in the non-aqueous solvent and is substantially free of any conjugate base, may be combined under conditions sufficient to produce a nanodispersion. The components may be combined in any convenient order. The components may be combined at any convenient temperature, e.g., room temperature or elevated temperatures, such as temperatures ranging from about 30 to about 95° C., about 50 to about 60° C., or about 70 to about 80° C. Certain of the components may be combined with each other, and then combined together, or all of the components may be combined at substantially the same time. Combination may include various manners of agitation or mixing, e.g., stirring, sonication, etc., in order to produce the desired nanodispersion.

As indicated above, an initial nanodispersion is prepared that includes docetaxel, an oil, a non-ionic surfactant, a non-aqueous solvent and an organic acid, wherein said organic acid is soluble in the non-aqueous solvent and is substantially free of any conjugate base. In certain embodiments, the initial nanodispersion is clear. By clear is meant that the nanodispersion is a translucent, if not transparent liquid, i.e., the liquid is pellucid. As such, the initial preparation is not cloudy. Further details regarding the nanodispersions that may be prepared from the docetaxel initial composition precursors are provided below.

In some embodiments, the present disclosure provides a method for making the non-aqueous, ethanol-free docetaxel nanodispersion formulation as disclosed herein, the method comprising combining docetaxel, an oil, a non-ionic surfactant, a non-aqueous solvent and an organic acid; and sterilizing the product thereof to provide the non-aqueous, ethanol-free docetaxel nanodispersion formulation.

The preparation methods can be carried out at certain temperature such as temperatures ranging from about 30° C. to about 95° C., about 50° C. to about 60° C., about 60° C. to about 70° C., or about 70° C. to about 80° C. Specific examples are provided in the Experimental section, below.

In some embodiments, the method for making the non-aqueous, ethanol-free docetaxel nanodispersion formulation as disclosed herein does not comprise the addition of water and/or ethanol, followed by removal thereof. Accordingly, since the non-aqueous, ethanol-free docetaxel nanodispersion formulation has not been contacted with either water or ethanol during the formulation process, it is substantially free of water (i.e, less than about 3%) and free of ethanol. In some embodiments, the formulation is essentially free of water (i.e, less than about 1%). In addition, in certain embodiments, the formulations do not have any detectable amount of ethanol. This results in a formulation which is stable and can be suitable for subjects having an adverse reaction to ethanol. In some embodiments, the formulations do not contain activated carbon.

Where desired, an amount of the nanodispersion may be loaded into an individual dosage container, e.g., vial, which holds the nanodispersion and keeps it sterile during shipping, storage, and handling. Before or during the loading stage, the nanodispersion can be passed through a sub-micron sterilizing filter, e.g., a 0.2 μm hydrophilic filter) which has a sufficiently small pore size to remove any bacteria or viruses. The sterilizing filters of interest include, but are not limited to hydrophilic filters. In some embodiments, the filter could be a CA (Cellulose Acetate) membrane filter, PTFE (Polytetrafluoroethylene) membrane filter, PVDF (Polyvinylidene fluoride or polyvinylidene difluoride) membrane filter or PES (Polyethersulfone) membrane filter.

As used herein, the term "vial" refers to any container that is used to hold the nanodispersion formulation. Many pharmaceutical vials are made of clear glass, which allows several advantages, including visual inspection of the enclosed drug (to ensure that it is still in a clean, non-caramelized, non-collapsed form, when it is ready for use) and of the container itself (to ensure that it does not have a hairline crack in one of the walls, which could jeopardize or destroy sterility of the enclosed drug). Various types of pharmaceutical vials are known. Single-chamber vials can be sealed with rubber or plastic plugs that will allow a hypodermic needle to be pushed through the rubber seal. Examples include any hydrolytically stable glass, such as a borosilicate Type I or soda-lime-silica Type II glass vial, having a suitable stopper (e.g., Teflon coating). Alternately, a single-chamber vial can be made of a brittle and easily breakable material, inside a sealed bag that can contain an aqueous solution (such as physiological saline or a dextrose solution, in an intravenous infusion bag); if this type of vial is broken, it will release its contents into the still-sealed bag, for mixing. In yet other embodiments, two-chamber vials or analogous structures, e.g., as described in Published United States Application Publication No. 2003/0099674 and U.S. Pat. No. 4,781,354 may be employed. Other methods for preparing the docetaxel formulations disclosed herein can be found in Published United States Application Publication No. 2011/0269829, the entirety of which is incorporated herein by reference.

Docetaxel Formulations and Methods of Use

Following preparation of the nanodispersion formulation, e.g., as described above, at the time of desired administration to a subject, a dosage amount of the nanodispersion may be combined with an aqueous medium to prepare a docetaxel diluted solution that is suitable for use. The dosage amount of the nanodispersion formulation may be combined with any suitable aqueous medium, where aqueous mediums of interest include, but are not limited to: deionized water, USP water for injection (WFI), salines, transfusion solutions, physiological solutions, etc. In some embodiments, the aqueous medium comprises an aqueous 0.9% sodium chloride solution or an aqueous 5% dextrose solution. The liquids to nanodispersion (high viscous liquid) ratio employed during preparation of the diluted solution may vary, and in certain embodiments ranges from 0.5 to 300, such as 1 to 100, 2 to 50 or 2 to 20, and including 2 to 10. In some instances, the dosage amount of nanodispersion formulation that is combined with the aqueous medium ranges from 100 to 1200 g, such as 300 to 600 g and the amount of aqueous medium that is combined with the dosage amount ranges from 100 to 1200 ml, such as 250 to 600 ml.

The docetaxel diluted solutions prepared from the nanodispersion formulations are liquid preparations that are a suspension of small particles (i.e., globules) of one liquid in a second liquid with which the first liquid will not mix. The water present in the docetaxel diluted solutions may be any convenient water, including deionized water, USP water for injection (WFI), etc.

The docetaxel diluted solutions include docetaxel, an oil, a non-ionic surfactant, a non-aqueous solvent and an organic acid, wherein said organic acid is soluble in the non-aqueous solvent and is substantially free of any conjugate base, and an aqueous medium. In certain embodiments, the docetaxel diluted solutions are clear. By clear is meant that the diluted solution is a translucent, if not transparent liquid, i.e., the liquid is pellucid. As such, the diluted solution is not cloudy, e.g., as a suspension may appear. Further details regarding the docetaxel diluted solutions that may be prepared from the docetaxel nanodispersion precursors are provided below. In some instances, the particle size of the final docetaxel diluted solutions ranges from about 3 to about 70 nm, such as about 5 to about 50 nm and including about 7 to about 30 nm, such as about 8 to about 15 nm. In some instances, any difference in particle size between the non-aqueous formulation and the docetaxel diluted solution is minimal, such that the particle sizes in the non-aqueous formulation and the docetaxel diluted solution are substantially the same. In some instances, any difference in particle size between the non-aqueous formulation and the docetaxel diluted solution is about 30 nm or less, such as about 20 nm or less, about 15 nm or less, about 10 nm or less, or about 5 nm or less. Without wishing to be bound by any one theory, it is contemplated that the inclusion of the oil in the nanodispersion formulations helps stabilize the diluted solution.

Where desired, the nanodispersion formulation may be stored for a period of time prior to combination with the aqueous medium. This storage time of the nanodispersion composition may vary, where storage times may be about 1 year or more, such as about 2 years or more, including about 3 years or more. While the storage conditions may vary, in certain instances the storage conditions are characterized by a temperature ranging from about 5 to about 60° C., e.g., about 5° C., such as about 8 to about 40° C., e.g., about 25° C. The activity of the docetaxel is substantially preserved during the storage period, such that the nanodispersion formulations are storage stable. As such, the activity of the docetaxel in the docetaxel diluted solution following storage is substantially the same as that in the nanodispersion prior to being combined with an aqueous medium, where the magnitude of any difference in activity between the non-aqueous formulation and the docetaxel diluted solution may be about 15% or less, such as about 10% or less, including about 5% or less.

As shown in Example 2, the nanodispersion formulation according the present disclosure is stable for more than about 3 months at about 40° C., or is stable for more than about 6 months at about 40° C. (see Example 3). In contrast, the formulations which contain lactic acid buffer (i.e., lactic acid with sodium lactate) rather than lactic acid alone show signs of deterioration during the same time period. The stability of the present nanodispersion formulations can be determined by methods known in the art, such as by measuring the percent deterioration of the docetaxel peak by HPLC or by measuring recovery rate for the docetaxel by HPLC. In some embodiments, the nanodispersion formulation exhibits a docetaxel recovery rate of more than about 95% after 6 months at about 40° C., or about 96% or more, or more than about 97% or more, or more than about 98% or more, or about 99% or more. The recovery rate is calculated based on the measured amount of docetaxel in the formulation, which is not necessarily the amount of docetaxel added to the formulation (thus eliminating any potential error from an impurity in the docetaxel).

The docetaxel diluted solutions that are produced upon dilution of the nanodispersion formulation with the aqueous medium can have a physiologically acceptable pH. In certain embodiments, the pH of the diluted solutions ranges from about 2.5 to about 8, such as from about 3 to about 7, including from about 3.5 to about 6. The docetaxel diluted solutions are clear (i.e., transparent) formulations. The concentration of docetaxel in the diluted solution may vary, ranging in some embodiments from about 0.05 to about 10 mg/ml, such as about 0.2 to about 3 mg/ml.

The combination protocol may vary, where agitation may be employed, e.g., by stirring, by kneading a bag that includes both the nanodispersion formulation and the aqueous medium.

Methods of using the docetaxel diluted solutions include administering an effective amount of the docetaxel diluted solution to a subject in order to treat the subject for a target condition of interest. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated, such as pain. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the diluted solutions disclosed herein can be parenterally administered to a subject. By "parenteral administration" is meant administration by a protocol that delivers a quantity of the diluted solutions to the subject, e.g., a patient suffering from a cellular proliferative disease, by a route other than the digestive tract. Examples of parenteral administration include, but are not limited to, intramuscular injection, intravenous injection, and the like. In certain embodiments, parenteral administration is by injection using an injection delivery device. The amount of diluted solutions that is administered to the subject may vary depending on a number of factors, such as patient specifics, nature of condition, etc.

In certain embodiments, the subject methods include a diagnostic step. Individuals may be diagnosed as being in need of the subject methods using any convenient protocol. In addition, individuals may be known to be in need of the subject methods, e.g., they are suffering from a target disease condition (e.g., cellular proliferative disease, prior to practicing the subject methods). Diagnosis or assessment of target condition can be performed using any convenient diagnostic protocol.

Methods of the invention may further include assessing the efficacy of the treatment protocol that includes administration of the docetaxel diluted solution. Assessing the efficacy of treatment may be performed using any convenient protocol.

The docetaxel diluted solutions of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Accordingly, provided herein are methods of administering an ethanol-free docetaxel liquid nanodispersion formulation to a subject, the method comprising: (a) combining the ethanol-free docetaxel nanodispersion formulation according to the present disclosure with an aqueous medium to provide an ethanol-free docetaxel diluted solution; and (b) administering the ethanol-free docetaxel diluted solution to the subject.

In some embodiments, the method of using the docetaxel nanodispersion formulation comprises the steps of: (a) aseptically withdrawing the desired amount of the docetaxel nanodispersion formulation (such as a formulation comprising about 20 mg docetaxel/mL) with a calibrated syringe, (b) injecting said formulation into a 250 mL infusion bag or bottle of either 0.9% sodium chloride solution or 5% dextrose solution to provide a diluted solution having a final docetaxel concentration of from about 0.3 mg/mL to about 0.74 mg/mL, and (c) administering said diluted solution to a patient. If a dose greater than 200 mg of docetaxel is required, one may use a larger volume of the infusion vehicle so that a concentration of 0.74 mg/mL docetaxel is not exceeded.

In certain embodiments, the volume of diluted solution that is administered to a subject may range from about 100 to about 1000 ml, such as about 200 to about 600 ml. The time period over which this volume is administered may vary, ranging from about 0.5 to about 6 hr, such as from about 1 to about 3 hr. Dosages administered to a subject during a given procedure may also vary, ranging in some instances from about 20 to about 500 mg/m$^2$, such as from about 50 to about 300 mg/m$^2$.

In determining whether to administer the diluted solution to a particular given subject, care will be taken to ensure that the formulation is not contraindicated for that subject. As such, symptoms of the subject may be assessed to ensure that administration of the diluted solution will not have adverse effects that outweigh any benefit that the diluted solution may provide.

Utility

The subject diluted solutions and methods find use in a variety of applications, including the treatment of subjects suffering from cellular proliferative disease conditions. Cellular proliferative diseases that may be treated with formulations of the invention include, but are not limited to: carcinomas, myelomas, neuroblastomas, or sarcomas, of the brain, breast, lung, colon, prostate or ovaries, as well as leukemias or lymphomas. Specific disease conditions of interest include, but are not limited to, human ovarian cancer, breast cancer, malignant lymphoma, lung cancer, melanoma, and Kaposi's sarcoma.

Kits

Also provided are kits that find use in practicing the subject methods, as described above. For example, kits for practicing the subject methods may include a quantity of the nanodispersion formulation, present in unit dosages, e.g., vials, or a multi-dosage format. As such, in certain embodiments, the kits may include one or more unit dosages (e.g., vials) of the nanodispersion formulation. The term "unit dosage", as used herein, refers to physically discrete units suitable as unitary dosages for human and animal subjects, each unit containing a predetermined quantity of the subject nanodispersion formulation calculated in an amount sufficient to produce the desired effect. The amount of the unit dosage of the subject formulation depends on various factors, such as the particular active agent employed, the effect to be achieved, and the pharmacodynamics associated with the active agent in the subject. In yet other embodiments, the kits may include a single multi-dosage amount of the formulation.

In certain embodiments, the kits may further include an amount of an aqueous medium suitable for use in productionof the docetaxel diluted solution. The aqueous medium may be any convenient aqueous medium, such as described above, present in any suitable container, e.g., an IV bag.

In some embodiments, the kits may include a syringe which is suitable to prepare the docetaxel diluted solution. A syringe with graduations is preferred to measure a certain amount of the docetaxel nanodispersion.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., one or more pieces of paper on which the information is printed, in the packaging of the kit, in a package insert, etc. The instructions may be present on a computer readable medium, e.g., diskette, CD, DVD, etc., on which the information has been recorded. The instructions may be present on a website, which may be used via the internet to access the information at a removed site. Other convenient means are possible and may be included in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

EXAMPLE 1

General Formulation

Nanodispersion Formulation

Taxane (e.g., anhydrous docetaxel or docetaxel trihydrate), oil (e.g., soybean oil), surfactant (e.g., polysorbate 80), non-aqueous solvent (e.g., polyethylene glycol 300, average molecule weight=300) and organic acid component (e.g., lactic acid or lactic acid mixture of 4:1 by wt lactic acid to sodium lactate) are placed into a beaker. The beaker is heated to 70-80° C. and the ingredients mixed via ultrasonic dispersion.

The resultant solution is poured into a vial through a 0.2 micron filter while applying nitrogen and the tube sealed. Optionally, steam treatment (95° C.×30 min.) can then be applied.

Diluted Solution

The resultant nanodispersion formulation is then placed into a test tube. Purified water was added and the tube was shaken by hand for about 20 seconds to obtain a clear solution. The particle size is then measured via a particle size distribution in the dynamic light scattering measurement protocol.

The various studies performed using nanodispersion formulations and diluted solutions prepared as described above are outlined in the Examples below.

EXAMPLE 2

Oil Studies

Nanodispersion samples were prepared according to Example 1 and 0.5 ml of the sample was added to 25 ml of 5% glucose solution in a glass centrifuge tube. The tube was shaken by hand for about 20 seconds. The diluted sample was evaluated by visual inspection for phase separation, color, clarity, consistency and particulates in the clear, glass tube.

Oil Study 1

In the following Example, all components were mixed, water was added, and the formulation was autoclaved then left at room temperature for four days. As shown in Table 1, when the ratio of soybean oil to docetaxel (by weight) is 1 (Entry (1)) or 2.5 (Entry (2)), there was no phase separation observed after 4 days.

TABLE 1

| Formulation A | (1) | (2) |
|---|---|---|
| Docetaxel | 4 | 4 |
| Soybean oil | 4 | 10 |
| Polysorbate 80 (GS) | 100 | 100 |
| Polyglycol (PG) | 90 | 90 |
| Glycerin | 10 | 10 |
| LA-Buffer (8:2) | 1 | 1 |
| Physical appearance of the dispersion sample (4 days later) | ○ | ○ |

○: Clear and free from particle matter
Δ: Very slightly cloudy
x: Slightly cloudy/cloudy/phase separation/precipitation Oil Study 2

As shown in Table 2, when the ratio of soybean oil to docetaxel (by weight) is three (Entry (2)), the quality of the nanodispersion declines.

TABLE 2

| Formulation B | (1) | (2) |
|---|---|---|
| Docetaxel trihydrate | 4 | 4 |
| MCT (NEOBEE 1053) | 8 | 12 |
| Polysorbate 80 (TO-10MV) | 95 | 95 |
| Lactic Acid Buffer (LA:70% LANa = 8:2) | 1 | 1 |
| PEG 300 (MG300) | 70 | 70 |
| Physical appearance of dispersion | ○ | x* |

○: Clear and free from particle matter
Δ: Very slightly cloudy
x: Slightly cloudy/cloudy/phase separation/precipitation
*gelatinous look Oil Study 3

The following docetaxel nanodispersion solutions were evaluated by visual inspection for phase separation, color, clarity, consistency and particulates in clear, glass tubes when they were prepared. In addition, 5.25 ml of each sample was combined with 250 ml of 0.9% sodium chloride solution or 5% glucose solution. The diluted solution was then visually inspected after 6 hours and 24 hours. The results are shown in Tables 3 and 4. The stability of the docetaxel diluted solution was increased by adding oil.

TABLE 3

| Formulation C | (1) | (2) | (3) | (4) |
|---|---|---|---|---|
| Docetaxel | 4 | 4 | 4 | 4 |
| MCT (NEOBEE 1053) | 0 | 0 | 4 | 4 |
| Polysorbate 80 (TO-10MV) | 100 | 100 | 100 | 100 |
| PEG 300 (MG300) | 40 | 40 | 40 | 40 |
| PEG 400 (MG400) | 10 | 60 | 10 | 60 |
| Lactic Acid Buffer | 1 | 1 | 1 | 1 |
| Physical appearance of dispersion (0 days) | ○ | ○ | ○ | ○ |
| Physical appearance of diluted solution (6 hrs) | ○~Δ | ○~Δ | ○ | ○ |
| Physical appearance of diluted solution (24 hrs) | x | x | Δ | Δ |

○: Clear and free from particle matter
Δ: Very slightly cloudy
x: Slightly cloudy/cloudy/phase separation/precipitation

TABLE 4

| Formulation D | (1) | (4) |
|---|---|---|
| Docetaxel trihyrate | 4 | 4 |
| Soybean oil | 0 | 4 |
| Polysorbate 80 (TO-10MV) | 95 | 95 |
| Lactic Acid Buffer LA:70% LANa = 8:2) | 1 | 1 |
| PEG 300 (MG300) | 70 | 70 |
| Physical appearance of diluted solution (6 hrs) | x x | ○ Δ |

○: Clear and free from particle matter
Δ: Very slightly cloudy
x: Slightly cloudy/cloudy/phase separation/precipitation Oil Study 4: Comparison Example Table 5 shows the stability of formulations provided using water in the formulation process (see US2011/0269829, section II: Docetaxel Formulations, A. Working example 1.). Particle size was measured before the water removal process.

TABLE 5

|  | Formulation E (1) | Formulation E (3) | Formulation F (1) | Formulation F (3) |
| --- | --- | --- | --- | --- |
| Docetaxel | 4 (200 mg) | 4 (200 mg) | 4 (200 mg) | 4 (200 mg) |
| Soybean oil | 10 (500 mg) | 4 (200 mg) | — | — |
| MCT* | — | — | 10 (500 mg) | 4 (200 mg) |
| Polysorbate 80 | 100 (5 g) | 100 (5 g) | 100 (5 g) | 100 (5 g) |
| PG | 100 (5 g) | 100 (5 g) | 100 (5 g) | 100 (5 g) |
| Lactic Acid Buffer (LA 155 mg, 70% LANa 95 mg) | 5 | 5 | 5 | 5 |
| Particle size (nm) | 17.5 (wide) | 12.8 | 14.7 (wide) | 12.1 |
| Physical appearance of dispersion after water removal (0 days) | Cloudy, phase separation | Transparent, clear | Transparent, clear | Transparent, clear |

*MCT: Nisshin O.D.O

EXAMPLE 3

PEG (Polyethylene Glycol)

Nanodispersion samples were prepared according to Example 1 and evaluated by visual inspection for phase separation, color, clarity, consistency and particulates in clear, glass vials.

PEG Study 1: Stability

The formulations shown in Table 6 were stored at 40° C./75% RH for 6 months (Formulation G, Entries (1), (2), and (3)) and 5° C. for 6 months (Formulation H, Entries (1), (2), and (3)). Table 6 shows that the formulations which used PEG 300, which has a melting point of −15° C. to −8° C., maintained transparency.

TABLE 6

|  | Formulation G (1)(2)(3) | Formulation H (1)(2)(3) |
| --- | --- | --- |
| Docetaxel trihydrate | 4 mg | 4 mg |
| MCT (NEOBEE 1053) | 4 | 4 |
| Polysorbate 80 (TO-10MV) | 95 | 95 |
| PEG 300 (MG300) | 70 | — |
| PEG 400 (MG400) | — | 70 |
| LA-Buffer (LA:70% LANa = 8:2) | 1 | 1 |
| Physical appearance of dispersion after 6 months at 40° C. | (1)(2)(3) Yellow/ Transparent/ Clear | (1)Yellow/ Transparent/ Clear (2)(3) Yellow/ Transparent/ |
| Physical appearance of dispersion after 6 months at 5° C. | (1)(2)(3) Yellow and cloudy. Floating subjects observed when temperature was still low. When the temperature was back to room temperature, it was Yellow/ Transparent/ Clear. | Slightly cloudy (1)(2)(3) Yellow and cloudy. Floating subjects were seen when the temperature was still low. When the temperature was back to room temperature, it was Yellow/ Transparent but still Cloudy and Ununiform. |

PEG Study 2: Solubility

Formulations of anhydrous docetaxel and either PEG 400 or PEG 300 were prepared and mixed using ultrasonic dispersion for 5 minutes at 70-80° C. 1 g of PEG 400 dissolved 25 mg of anhydrous docetaxel. 1 g of PEG 400 did not fully dissolve 50 mg of anhydrous docetaxel. 1 g of PEG 300 dissolved 100 mg of anhydrous docetaxel. Accordingly, PEG 300 was able to better solubilize anhydrous docetaxel.

PEG Study 3: Polysorbate/PEG Ratio

As shown in Table 7, when the ratio of polysorbate to PEG is greater than or equal to 1 (i.e., the amount of polysorbate is greater than or equal to the amount of PEG), the formulations exhibit stability compared to formulations having less PEG with respect to polysorbate.

TABLE 7

|  | Formulation C (4) | Formulation C (5) | Formulation C (6) | Formulation I (4) | Formulation I (5) | Formulation I (6) |
| --- | --- | --- | --- | --- | --- | --- |
| Docetaxel | 4 | 4 | 4 | | | |
| Docetaxel trihydrate | | | | 4 | 4 | 4 |
| MCT (NEOBEE 1053) | 4 | 4 | 4 | 4 | 4 | 4 |
| Polysorbate 80 (TO-10MV) | 100 | 100 | 100 | 95 | 95 | 95 |
| PEG300 (MG300) | 40 | 40 | 20 | 100 | 50 | 0 |
| PEG400 (MG400) | 10 | 60 | 80 | 0 | 50 | 100 |
| LA-Buffer | 1 | 1 | 1 | 1 | 1 | 1 |
| Total | 159 | 209 | 209 | 204 | 204 | 204 |
| Ratio Polysorbate/PEG | 2 | 1 | 1 | 0.95 | 0.95 | 0.95 |

TABLE 7-continued

|  | Formulation C (4) | Formulation C (5) | Formulation C (6) | Formulation I (4) | Formulation I (5) | Formulation I (6) |
|---|---|---|---|---|---|---|
| Physical appearance of dispersion after 0 day | ○ | ○ | ○ | x Slightly cloudy | x Slightly Cloudy | ○ |
| Physical appearance of dispersion after 1 day | ○ | x phase separation | x phase separation | x phase separation | x phase separation | x phase separation slightly |
| Physical appearance of dispersion after 6 days |  |  |  | x | x | x phase separation |

○: Clear and free from particle matter
Δ: Very slightly cloudy
x: Slightly cloudy/cloudy/phase separation/precipitation PEG Study 4: Polysorbate/PEG Ratio (No API)

In Tables 8, 9 and 10, when the ratio of polysorbate to PEG is greater than or equal to 0.95 or 1 (i.e., the amount of polysorbate is greater than or about equal to the amount of PEG), the formulations exhibit stability compared to formulations having more PEG with respect to polysorbate (no taxane was added in Tables 8 and 9).

TABLE 8

| Formulation J | (1) | (2) | (3) | (4) | (5) | (6) | (7) | (8) | (9) | (10) |
|---|---|---|---|---|---|---|---|---|---|---|
| Ratio Polysorbate/PEG | 2 | 1 |  |  | 0.95 |  | 0.8 | 0.33 | 1.33 | 4 |
| Polysorbate 80 (TO-10MV) | 100 | 100 | 100 | 95 | 95 | 95 | 8 | 8 | 80 | 80 |
| PEG 300 (MG300) | 40 | 40 | 20 | 100 | 50 | 0 | 10 | 24 | 0 | 0 |
| PEG 400 (MG400) | 10 | 60 | 80 | 0 | 50 | 100 | 0 | 0 | 60 | 20 |
| Physical appearance of dispersion after 0 day | ○ | ○ | ○ | ○ | ○ | Δ | x | x | ○ | ○ |
| Physical appearance of dispersion after 5 days | ○ | ○ | ○ | x | x | x | x | x | ○ | ○ |

○: Clear and free from particle matter
Δ: Very slightly cloudy
x: Slightly cloudy/cloudy/phase separation/precipitation

TABLE 9

| Formulation K | 1 | 2 | 3 | 4 | 5 | 6 | 7 | 8 | 9 | 10 | 11 |
|---|---|---|---|---|---|---|---|---|---|---|---|
| Ratio Polysorbate/PEG |  |  | 0.33 |  |  |  |  | 0.67 |  |  | 1 |
| PEG 300/400 (MG300/400) | 0/100 | 25/75 | 50/50 | 75/25 | 100/0 | 0/100 | 25/75 | 50/50 | 75/25 | 100/0 | 75/25 |
| Polysorbate 80 (TO-10MV) | 8 | 8 | 8 | 8 | 8 | 16 | 16 | 16 | 16 | 16 | 16 |
| PEG 300 (MG300) | 0 | 6 | 12 | 18 | 24 | 0 | 6 | 12 | 18 | 24 | 12 |
| PEG 400 (MG400) | 24 | 18 | 12 | 6 | 0 | 24 | 18 | 12 | 6 | 0 | 4 |
| Physical appearance of dispersion after 0 day | x | x | x | x | x | x | x | x | x | x | ○ |

○: Clear and free from particle matter
Δ: Very slightly cloudy
x: Slightly cloudy/cloudy/phase separation/precipitation

TABLE 10

| Formulation L | (1) | (2) | (3) | (4) |
|---|---|---|---|---|
| Docetaxel trihydrate | 4 | 4 | 4 | 4 |
| MCT (NEOBEE 1053) | 0 | 0 | 4 | 4 |
| Polysorbate 80 (TO-10MV) | 95 | 95 | 95 | 95 |
| PEG 300 (MG300) | 40 | 85 | 40 | 85 |
| PEG 400 (MG400) | 10 | 0 | 10 | 0 |
| Lactic Acid Buffer | 1 | 1 | 1 | 1 |
| Total | 150 | 185 | 154 | 189 |
| Polysorbate/PEG Ratio | 1.9 | 1.12 | 1.9 | 1.12 |
| Physical appearance of dispersion after 0 day | ○ | ○ | ○ | ○ |
| Physical appearance of dispersion after 7 days | ○ | ○ | ○ | ○ |

○: Clear and free from particle matter
Δ: Very slightly cloudy
x: Slightly cloudy/cloudy/phase separation/precipitation PEG Study 5: Polysorbate/PEG Ratio Tables 11 and 12 show that the oil contributes to the stability of the docetaxel nanodispersion.

TABLE 11

| Formulation M | (1) |
|---|---|
| Docetaxel trihydrate | 4 |
| MCT (NEOBEE 1053) | 4 |
| Polysorbate 80 (TO-10MV) | 95 |
| PEG 300 (MG300) | 70 |
| Lactic Acid Buffer | 1 |
| Total | 174 |
| Polysorbate/PEG Ratio | 1.36 |
| Physical appearance of dispersion after 5 days | ○ |

○: Clear and free from particle matter
Δ: Very slightly cloudy
x: Slightly cloudy/cloudy/phase separation/ precipitation

TABLE 12

| Formulation N | (4) | (6) |
|---|---|---|
| Docetaxel trihydrate | 4 | 4 |
| MCT (NEOBEE 1053) | 0 | 0 |
| Polysorbate 80 (TO-10MV) | 95 | 95 |
| PEG 300 (MG300) | 70 | 85 |
| Lactic Acid Buffer | 1 | 1 |
| Polysorbate/PEG Ratio | 1.36 | 1.12 |
| Physical appearance of dispersion after 0 days | ○ | Δ |
| Physical appearance of dispersion after 1 days | ○ | ○ |

○: Clear and free from particle matter
Δ: Very slightly cloudy
x: Slightly cloudy/cloudy/phase separation/precipitation PEG Study 6: PEG and PG (Polyglycol) Comparison Table 13 shows that even with a polysorbate/PG ratio greater than 1, the formulation did not satisfy the desired quality level.

TABLE 13

| Formulation O | (1) |
|---|---|
| Docetaxel trihydrate | 4 (120 mg) |
| MCT (NEOBEE 1053) | 4 (120 mg) |
| Polysorbate 80 (TO-10MV) | 95 (2.85 g) |
| Lactic Acid Buffer (LA:70% LANa = 8:2) | 1 (30 mg) |
| Polyglycol | 70 (2.1 g) |
| Polysorbate/Polyglycol Ratio | 1.36 |
| Physical appearance of dispersion after 0 days | Δ |
| Physical appearance of dispersion after 1 days | x |

○: Clear and free from particle matter
Δ: Very slightly cloudy
x: Slightly cloudy/cloudy/phase separation/precipitation Table 14 shows that even when the polysorbate/polyglycol&PEG ratio was over 1, when polyglycol was added, the quality of the nanodispersion declined.

TABLE 14

| Formulation P | (1) | (2) |
|---|---|---|
| Docetaxel trihydrate | 4 (120 mg) | 4 (120 mg) |
| MCT (NEOBEE 1053) | 4 (120 mg) | 4 (120 mg) |
| Polysorbate 80 (TO-10MV) | 95 (2.85 g) | 95 (2.85 g) |
| Lactic Acid Buffer (LA:70% LANa = 8:2) | 1 (30 mg) | 1 (30 mg) |
| PEG 300 (MG300) | 40 (1.2 g) | 30 (900 mg) |
| Polyglycol | 0 | 40 (1.2 g) |
| Polysorbate/Polyglycol&PEG Ratio | 0.42 | 1.36 |
| Physical appearance of dispersion after 2 days | Slightly cloudy | Cloudy, Particulates |

TABLE 14-continued

| Formulation P | (1) | (2) |
|---|---|---|
| Physical appearance of diluted solution (3 hr) | o, Δ (2 samples) | N/A | o: Clear and free from particle matter
Δ: Very slightly cloudy
x: Slightly cloudy/cloudy/phase separation/precipitation

EXAMPLE 5

Buffering Agent

Lactic Acid Study 1: Lactic Acid and Lactic Acid Buffer

Lactic acid lowered the pH further than lactic acid buffer (docetaxel is stable at pH 3.0-4.0) (Table 15).

TABLE 15

| Formulation Q | (1) | (2) | (3) | (4) |
|---|---|---|---|---|
| Docetaxel | — | 4 (120 mg) | — | — |
| Docetaxel trihydrate | 4 (120 mg) | — | — | — |
| MCT (NEOBEE 1053) | 4 (120 mg) | 4 (120 mg) | 4 (200 mg) | 4 (200 mg) |
| Polysorbate 80 (TO-10MV) | 95 (2.85 g) | 95 (2.85 g) | 95 (4.75 g) | 95 (4.75 g) |
| PEG 300 (MG300) | 70 (2.1 g) | 70 (2.1 g) | 70 (3.5 g) | 70 (3.5 g) |
| Lactic Acid Buffer (LA:90% LANa = 8:2) | — | — | — | 1 (50 mg) |
| Lactic Acid | 0.8 (24 mg) | 0.8 (24 mg) | 0.8 (40 mg) | — |
| Physical appearance of dispersion | o two bubbles were seen | o two bubbles were seen | o | o |
| pH of diluted solution | 3.19 | 3.16 | 3.15 | 3.43 | o: Clear and free from particle matter
Δ: Very slightly cloudy
x: Slightly cloudy/cloudy/phase separation/precipitation

EXAMPLE 6

Water Free Formulation

Lactic Acid Study 1: LA and LA buffer

The formulations in Tables 16 and 17 exhibit stability over a six month period. In the Tables, the lactic acid formulations exhibited an enhanced stability when compared to the lactic acid buffer formulations (Table 16 vs Table 17).

TABLE 16

| | Formulation R | Formulation S (1)(2) | Formulation G (1)-(3) | Formulation T | Formulation U (2) | Formulation V |
|---|---|---|---|---|---|---|
| Docetaxel | — | — | — | — | — | 4 |
| Docetaxel trihydrate | 4 | 4 | 4 | 4 | 4 | — |
| NEOBEE 1053 | 4 | 4 | 4 | 4 | 4 | 4 |
| Polysorbate 80 (TO-10MV) | 95 | 95 | 95 | 95 | — | — |
| Polysorbate 80 (GS) | — | — | — | — | 95 | 95 |
| PEG 300 (MG300) | 70 | 70 | 35 + 35 | 35 + 35 | 70 | 70 |
| Lactic Acid Buffer (LA:70% LANa = 8:2) | 1 | 1 (100 mg) | 1 (100 mg) | — | — | — |
| Lactic Acid Buffer (LA:90% LANa = 8:2) | — | — | — | 1 | — | — |
| Dehydrated Lactic Acid Buffer (LA:90% LANa = 8.4:1.6) | — | — | — | — | 0.8 | 0.8 |
| Docetaxel recovery rate after 6 months | 86.7-89.3% | 86.7-89.3% | 86.4-88.2% | (1 month) 95.8% | 94.5% | 91.1% |
| Degradation peak after 6 months | 3.3-3.6% | 3.3-3.6% | 2.6-2.9% | (1 month) 1.7% | 1.9% | 3.9% |
| pH of docetaxel nanodispersion | 3.50 | 3.50 | 3.61-3.62 | (1 month) 3.53 | 3.55 | 3.54 |
| pH of diluted solution | 3.69-3.70 | 3.69-3.70 | 3.77-3.80 | — | — | — |

TABLE 17

| | Formulation W (1)-(3) | Formulation X (1)-(3) | Formulation Y (1)-(3) | Formulation Z (1)-(3) |
|---|---|---|---|---|
| Docetaxel | 4 | — | 4 | — |
| Docetaxel trihydrate | — | 4 | — | 4.27 |
| NEOBEE 1053 | 4 | 4 | — | — |
| Soybean oil | — | — | 4 | 4 |
| Polysorbate 80 (GS) | 95 | 95 | 95 | 95 |
| PEG 300 (MG300) | 70 | 70 | 70 | 70 |
| Lactic Acid | 0.8 | 0.8 | 0.8 | 0.8 |
| Docetaxel recovery rate after 6M | 96.9-98.0% | 99.3-100.7% | 101.6-102.3% | 101.4-102.4% |
| Degradation peak after 6 months | 1.0-1.4% | 0.8% | 0.1% | 0.1% |
| pH of docetaxel nanodispersion | 3.07-3.10 | 3.01-3.02 | 3.02-3.06 | 3.05-3.11 |
| pH of diluted solution | — | 3.54-3.57 | 3.54-3.57 | 3.54-3.57 |

EXAMPLE 1a

Docetaxel Nanodispersion Formulations Using Lactic Acid

Docetaxel, an oil, a non-ionic surfactant, a non-aqueous solvent and lactic acid were placed into a beaker. The beaker was heated to 70-80° C., the ingredients mixed via ultrasonic dispersion, the resultant solution was added to a vial tube through a 0.2 μm filter while applying nitrogen and the tube was sealed.

To determine particle size, a non-aqueous composition as prepared using the general procedure outlined above was placed into a test tube. Purified water was added and the tube was shaken by hand for about 20 seconds to obtain a clear solution. When the particle size was measured via a particle size distribution in the dynamic light scattering measurement protocol, the average particle size was observed to be between about 8 and about 13 nm.

Specific formulations (in mg) as prepared via the general method disclosed above are summarized in Table 1a, below.

TABLE 1a

| | Docetaxel | | Oil | | | Surfactant | Solvent | |
| | | | MCT | | | Polysorbate | PEG 300 | Lactic |
| No. | Anhydrous | Trihydrate | (NEOBEE ® #1053) | MCT (Panacet ®) | Soybean Oil | 80 | (MG-300) | Acid |
|---|---|---|---|---|---|---|---|---|
| 1A | | 4 | 4 | | | 95 | 70 | 0.8 |
| 1B | | 4 | 4 | | | 95 | 70 | 0.8 |
| 1C | | 4 | 4 | | | 95 | 70 | 0.8 |
| 2A | 4 | | 4 | | | 95 | 70 | 0.8 |
| 2B | 4 | | 4 | | | 95 | 70 | 0.8 |
| 2C | 4 | | 4 | | | 95 | 70 | 0.8 |
| 3A | 4 | | 4 | | | 95 | 70 | 0.8 |
| 3B | | 4 | 4 | | | 95 | 70 | 0.8 |
| 4A | | 4.27* | | | 4 | 95 | 70 | 0.8 |
| 4B | | 4.27* | | | 4 | 95 | 70 | 0.8 |
| 4C | | 4.27* | | | 4 | 95 | 70 | 0.8 |
| 5A | 4 | | | | 4 | 95 | 70 | 0.8 |
| 5B | 4 | | | | 4 | 95 | 70 | 0.8 |
| 5C | 4 | | | | 4 | 95 | 70 | 0.8 |
| 6 | 4 | | | 4 | | 95 | 70 | 0.8 |

*4.27 mg Docetaxel trihydrate is equivalent to 4 mg of docetaxel.

EXAMPLE 2a

Docetaxel Nanodispersion Formulations Using Lactic Acid Buffer

Docetaxel formulations were prepared according to the general procedure outlined in Example 1a using 1 mg of lactic acid buffer (0.80 mg Lactic acid and 0.20 mg 90% sodium lactate) rather than lactic acid. These formulations are summarized Table 2a, below.

TABLE 2a

| No. | Docetaxel Anhydrous | Docetaxel Trihydrate | Oil MCT (NEOBEE ® #1053) | Surfactant Polysorbate 80 (refined grade) | Surfactant Polysorbate 80 (TO-10MV) | Solvent PEG 300 (MG-300)*** | Solvent PEG 400 (MG-400)**** |
|---|---|---|---|---|---|---|---|
| 7* | 4 |   | 4 | 95 |   | 70 |   |
| 8* |   | 4 | 4 | 95 |   | 70 |   |
| 9A# | 4 |   | 4 |   | 95 | 70 |   |
| 9B# | 4 |   | 4 | 95 |   | 70 |   |
| 9C** |   | 4 | 4 |   | 95 | 70 |   |
| 9D**# |   | 4 | 4 | 95 |   | 70 |   |
| 10A† |   | 4 | 4 |   | 95 |   | 70 |
| 10B† |   | 4 | 4 |   | 95 |   | 70 |
| 10C† |   | 4 | 4 |   | 95 |   | 70 |
| 11A† |   | 4 | 4 |   | 95 | 70 |   |
| 11B† |   | 4 | 4 |   | 95 | 70 |   |
| 11C† |   | 4 | 4 |   | 95 | 70 |   |
| 12A† |   | 4 | 4 |   | 95 | 70 |   |
| 12B† |   | 4 | 4 |   | 95 | 70 |   |
| 12C† |   | 4 | 4 |   | 95 | 70 |   |
| 13† |   | 4 | 4 |   | 95 | 70 |   |

*Dehydrated 90% sodium lactate by infrared radiation
**Steam treatment (95° C. × 30 min) was applied
***Average molecule weight = 300
****Average molecule weight = 400
†0.80 mg Lactic acid and 0.20 mg 70% sodium lactate
0.80 mg Lactic acid and 0.20 mg 90% sodium lactate

EXAMPLE 3a

Stability Study

The docetaxel recovery rate, percent degradation peak (as measured by HPLC) and formulation pH were measured at one month, three months and six months at 40° C. pH was measured by mixing 3 ml of water and 750 ml of docetaxel nanodispersion sample. The results from this stability study are shown in Table 3a, below. Each formulation having lactic acid rather than either lactic acid buffer or lactic acid buffer from dehydrated sodium lactate showed a significant increase in stability.

TABLE 3a

| No. | 0 month Docetaxel (mg) | 0 month Degradation Peak % | 0 month pH | 1 month Recovery rate % (against 0 month) | 1 month Degradation Peak % | 1 month pH | 3 months Recovery rate % (against 0 month) | 3 months Degradation Peak % | 3 months pH | 6 months Recovery rate % (against 0 month) | 6 months Degradation Peak % | 6 months pH |
|---|---|---|---|---|---|---|---|---|---|---|---|---|
| 6 | 3.722 | None | 3.12 | 98.3 | None | 3.10 |   |   |   |   |   |   |
| 1A | 3.570 | None | 3.06 | 100.8 | None | 3.04 | 98.0 | 0.20 | 3.03 | 99.3 | 0.8 | 3.01 |
| 1B | 3.550 | None | 3.09 | 102.1 | None | 3.03 | 98.1 | 0.30 | 3.05 | 100.7 | 0.8 | 3.01 (3.57*) |
| 1C | 3.570 | None | 3.08 | 101.6 | None | 3.03 | 97.9 | 0.30 | 3.04 | 100.5 | 0.8 | 3.02 (3.54*) |
| 7 | 3.750 | None | 3.27 | 97.3 | 1.1 | 3.41 | 94.7 | 2.40 | 3.47 | 91.1 | 3.9 | 3.54 |
| 8 | 3.542 | 0.20 | 3.32 | 96.5 | 1.9 | 3.45 | 92.7 | 2.20 | 3.49 | 94.5 | 1.9 | 3.55 |
| 2A | 3.800 | None | 3.04 | 97.4 | None | 3.04 (3.63*) | 97.3 | 0.40 | 3.03 (3.55*) | 96.9 | 1.4 | 3.07 |
| 2B | 3.784 | None | 3.05 | 99.4 | None | 3.03 (3.59*) | 97.6 | 0.30 | 3.06 (3.56*) | 97.0 | 1.0 | 3.10 |
| 2C | 3.810 | None | 3.04 | 98.1 | None | 3.03 (3.57*) | 98.1 | 0.40 | 3.02 (3.55*) | 98.0 | 1.1 | 3.07 |
| 3A | 3.805 | None | 3.04 | 97.5 | None | 3.05 | 96.8 | None | 3.07 |   |   |   |
| 3B | 3.635 | None | 3.08 | 97.4 | None | 3.05 | 96.8 | None | 3.07 |   |   |   |
| 9A | 3.840 | None | 3.44 | 95.3 | 2.1 | 3.57 | 90.2 | 2.50 | 3.60 |   |   |   |

TABLE 3a-continued

| | 0 month | | | 1 month | | | 3 months | | | 6 months | | |
|---|---|---|---|---|---|---|---|---|---|---|---|---|
| No. | Docetaxel (mg) | Degradation Peak % | pH | Recovery rate % (against 0 month) | Degradation Peak % | pH | Recovery rate % (against 0 month) | Degradation Peak % | pH | Recovery rate % (against 0 month) | Degradation Peak % | pH |
| 9B | 3.640 | None | 3.38 | 96.5 | 1.9 | 3.43 | 91.8 | 1.90 | 3.46 | | | |
| 9C | 3.670 | None | 3.44 | 95.5 | 1.6 | 3.56 | 88.4 | 3.40 | 3.57 | | | |
| 9D | 3.650 | None | 3.38 | 96.2 | 1.4 | 3.41 | 87.6 | 4.70 | 3.44 | | | |
| 10A | 3.766 | 0.20 | | 96.3 | 2.4 | 3.54 | 90.2 | 2.90 | 3.53 | 88.7 | 2.1 | 3.60 (3.77*) |
| 10B | 3.722 | 0.20 | | 96.7 | 2.1 | 3.57 | 90.9 | 2.80 | 3.57 | 87.4 | 2.2 | 3.63 (3.78*) |
| 10C | 3.750 | 0.20 | | 96.4 | 2.5 | 3.56 | 91.3 | 2.80 | 3.56 | 88.2 | 2.2 | 3.62 (3.76*) |
| 11A | 3.740 | 0.20 | | 96.9 | 2.0 | 3.52 | 91.2 | 3.40 | 3.55 | 86.4 | 2.9 | 3.61 (3.77*) |
| 11B | 3.654 | 0.20 | | 97.9 | 1.9 | 3.55 | 91.6 | 3.10 | 3.55 | 88.0 | 2.7 | 3.61 (3.78*) |
| 11C | 3.732 | 0.20 | | 97.0 | 2.2 | 3.55 | 90.7 | 3.30 | 3.55 | 88.2 | 2.6 | 3.62 (3.80*) |
| 12A | 3.615 | 0.10 | 3.64* | 95.4 | 2.8 | 3.39 | 95.6 | 4.00 | 3.39 | 87.5 | 3.5 | 3.50 (3.70) |
| 12B | 3.627 | 0.20 | 3.62* | 95.6 | 2.8 | 3.38 | 96.4 | 4.00 | 3.37 | 89.3 | 3.3 | 3.50 (3.69*) |
| 12C | 3.078 | 15.00 | 3.61* | 95.6 | 18.4 | 3.38 | 96.5 | 20.30 | 3.37 | 87.2 | 20.3 | 3.50 (3.69*) |
| 13 | 3.660 | 0.10 | | 94.7 | 2.6 | 3.41 | 93.8 | 4.00 | 3.42 | 86.7 | 3.6 | 3.50 (3.70*) |
| 4A | 3.676 | None | 3.03 | 100.4 | None | 3.03 | 101.0 | 0.1 | 3.07 (3.54*) | | | |
| 4B | 3.618 | 0.10 | 3.02 | 101.4 | None | 3.02 | 101.4 | 0.1 | 3.05 (3.56*) | | | |
| 4C | 3.632 | 0.10 | 3.01 | 100.4 | None | 3.01 | 102.4 | 0.1 | 3.11 (3.57*) | | | |
| 5A | 3.746 | None | 3.04 | 101.9 | None | 3.04 | 102.2 | 0.1 | 3.06 (3.57*) | | | |
| 5B | 3.770 | None | 3.04 | 101.7 | None | 3.02 | 102.3 | 0.1 | 3.05 (3.54*) | | | |
| 5C | 3.732 | None | 3.02 | 102.3 | None | 3.01 | 101.6 | 0.1 | 3.02 (3.54*) | | | |

*pH of docetaxel diluted solution.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A non-aqueous, ethanol-free taxane liquid formulation comprising:
    a taxane;
    an oil;
    a non-ionic surfactant;
    a non-aqueous solvent; and
    an organic acid component;
    wherein the organic acid component is soluble in the non-aqueous solvent and the amount by weight of non-ionic surfactant is equal to or greater than the amount by weight of non-aqueous solvent.

2. The formulation according to claim 1, wherein the taxane is present in an amount ranging from about 0.5 to about 5 wt %.

3. The formulation according to claim 1, wherein the taxane is present in about 2 wt %.

4. The formulation according to claim 1, wherein the taxane is paclitaxel.

5. The formulation according to claim 1, wherein the taxane is docetaxel.

6. The formulation according to claim 3, wherein the taxane is anhydrous docetaxel.

7. The formulation according to claim 3, wherein the taxane is docetaxel trihydrate.

8. The formulation according to claim 1, wherein the oil is selected from the group consisting of synthetic oils, vegetable oils, tocopherols and combinations thereof.

9. The formulation according to claim 8, wherein the oil is selected from the group consisting of soybean oil, olive oil, sesame oil, corn oil, a medium chain triglyceride, a tocopherol or derivative thereof and combinations thereof.

10. The formulation according to claim 1, wherein the oil is present in an amount ranging from about 1 to about 20 wt %.

11. The formulation according to claim 10, wherein the oil is soybean oil.

12. The formulation according to claim 11, wherein the soybean oil is present in an amount ranging from about 1 to about 5 wt %.

13. The formulation according to claim 10, wherein the oil is a medium chain triglyceride.

14. The formulation according to claim 13, wherein the medium chain triglyceride is present in an amount ranging from about 1 to about 5 wt %.

15. The formulation according to claim 1, wherein the non-ionic surfactant is present in an amount ranging from about 40 to about 75 wt %.

16. The formulation according to claim 15, wherein the non-ionic surfactant is present in an amount ranging from about 50 to about 60 wt %.

17. The formulation according to claim 1, wherein the non-ionic surfactant is polysorbate 80.

18. The formulation according to claim 1, wherein the non-aqueous solvent is present in an amount ranging from about 20 to about 60 wt %.

19. The formulation according to claim 18, wherein the non-aqueous solvent is present in an amount ranging from about 35 to about 45 wt %.

20. The formulation according to claim 1, wherein the non-aqueous solvent is polyethylene glycol.

21. The formulation according to claim 20, wherein the polyethylene glycol has a melting point of less than 0° C.

22. The formulation according to claim 1, wherein the organic acid component is present in an amount ranging from 0.3 to 3 wt %.

23. The formulation according to claim 22, wherein the organic acid component is present in an amount ranging from 0.5 to 1 wt %.

24. The formulation according to claim 1, wherein the organic acid component is an organic acid.

25. The formulation according to claim 24, wherein the organic acid is selected from the group consisting of lactic acid and acetic acid.

26. The formulation according to claim 25, wherein the organic acid is lactic acid.

27. The formulation according to claim 26, wherein the lactic acid is present in about 0.8 wt %.

28. The formulation according to claim 1, wherein the organic acid component is an organic acid buffer.

29. The formulation according to claim 28, wherein the organic acid buffer is lactic acid buffer.

30. The formulation according to claim 29, wherein the lactic acid buffer is present in about 1 wt %.

31. The formulation according to claim 1, wherein the amount by weight of oil is equal to or less than about 2.5 times the amount of taxane.

32. The formulation according to claim 1, wherein the ratio by weight of taxane to oil is from about 1:0.5 to about 1:2.5.

33. A non-aqueous, ethanol-free docetaxel liquid formulation comprising:
   docetaxel;
   soybean oil in an amount ranging from about 1 to about 5 wt %;
   polysorbate 80 in an amount ranging from about 50 to about 60 wt %;
   polyethylene glycol in an amount ranging from about 35 to about 45 wt %; and
   lactic acid or lactic acid buffer in an amount ranging from 0.3 to 1 wt %;
   wherein the amount by weight of non-ionic surfactant is about equal to or greater than the amount by weight of non-aqueous solvent.

34. A non-aqueous, ethanol-free docetaxel liquid formulation comprising:
   docetaxel;
   a medium chain triglyceride in an amount ranging from about 1 to about 5 wt %;
   polysorbate 80 in an amount ranging from about 50 to about 60 wt %;
   polyethylene glycol in an amount ranging from about 35 to about 45 wt %; and
   lactic acid or lactic acid buffer in an amount ranging from 0.3 to 1 wt %;
   wherein the amount by weight of non-ionic surfactant is about equal to or greater than the amount by weight of non-aqueous solvent.

35. The formulation according to claim 33, wherein the docetaxel is anhydrous docetaxel.

36. The formulation according to claim 33, wherein the docetaxel is docetaxel trihydrate.

37. The formulation according to claim 33, wherein the docetaxel is present in an amount ranging from about 0.5 to about 5 wt %.

38. The formulation according to claim 37, wherein the docetaxel is present in about 2 wt %.

39. The formulation according to claim 33, wherein the polyethylene glycol has a melting point of less than 0° C.

40. The formulation according to claim 33, wherein the ratio by weight of docetaxel to oil is from 1:0.5 to 1:2.5.

41. The formulation according to claim 1, wherein the ethanol-free taxane liquid formulation has a pH of less than about 3.5.

42. The formulation according to claim 1, wherein the formulation is stable for more than 6 months at 40° C.

43. The formulation according to claim 1, wherein the formulation exhibits a taxane recovery rate of greater than 95% after 6 months at 40° C.

44. The formulation according to claim 1, wherein the formulation forms particles of less than about 20 nm when combined with an aqueous medium.

45. A method of administering an ethanol-free taxane liquid formulation to a subject, the method comprising:
   (a) combining the ethanol-free taxane formulation according to claim 1 with an aqueous medium to provide an ethanol-free taxane diluted solution; and
   (b) administering the ethanol-free taxane diluted solution to the subject.

46. A kit comprising:
   (a) a vial containing the ethanol-free taxane formulation according to claim 1; and
   (b) instructions for using the ethanol-free taxane formulation.

47. The kit according to claim 46, further comprising (c) an aqueous medium.

48. The formulation according to claim 19, wherein the non-aqueous solvent is polyethylene glycol having an average molecular weight of 1000 or less.

49. The non-aqueous, ethanol-free taxane liquid formulation of claim 1, wherein
   the taxane is anhydrous docetaxel or a hydrate thereof;
   the oil is soybean oil in an amount ranging from about 1 to about 5 wt%;
   the non-ionic surfactant is polysorbate 80 in an amount ranging from about 50 to about 60 wt%; and
   the non-aqueous solvent is polyethylene glycol having an average molecular weight of 1000 or less, and in an amount ranging from about 35 to about 45 wt%.

50. A method of administering an ethanol-free taxane liquid formulation to a subject, the method comprising:

(a) combining the ethanol-free taxane formulation according to claim 49 with an aqueous medium to provide an ethanol-free taxane diluted solution; and
(b) administering the ethanol-free taxane diluted solution to the subject.

51. The formulation according to claim 49, wherein the formulation forms particles of less than about 20 nm when combined with an aqueous medium.

\* \* \* \* \*